US010406227B2

(12) United States Patent
Chow et al.

(10) Patent No.: US 10,406,227 B2
(45) Date of Patent: *Sep. 10, 2019

(54) PHOTOACTIVATED MOLECULES FOR LIGHT-INDUCED MODULATION OF THE ACTIVITY OF ELECTRICALLY EXCITABLE CELLS AND METHODS OF USING SAME

(71) Applicants: University of Southern California, Los Angeles, CA (US); California Institute of Technology, Pasadena, CA (US)

(72) Inventors: Robert H. Chow, Pasadena, CA (US); Mark S. Humayun, Glendale, CA (US); Harry B. Gray, Pasadena, CA (US); Robert H. Grubbs, South Pasadena, CA (US); Dennis A. Dougherty, Pasadena, CA (US); Mark E. Thompson, Anaheim, CA (US); Lionel E. Cheruzel, San Jose, CA (US); Melanie A. Yen, Pasadena, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/650,208

(22) PCT Filed: Dec. 18, 2013

(86) PCT No.: PCT/US2013/076297
§ 371 (c)(1),
(2) Date: Jun. 5, 2015

(87) PCT Pub. No.: WO2014/100283
PCT Pub. Date: Jun. 26, 2014

(65) Prior Publication Data
US 2015/0328313 A1  Nov. 19, 2015

Related U.S. Application Data

(60) Provisional application No. 61/905,056, filed on Nov. 15, 2013, provisional application No. 61/775,377, filed on Mar. 8, 2013, provisional application No. 61/762,793, filed on Feb. 8, 2013, provisional application No. 61/749,692, filed on Jan. 7, 2013, provisional application No. 61/739,597, filed on Dec. 19, 2012.

(51) Int. Cl.
*A61K 41/00* (2006.01)
*C12N 13/00* (2006.01)
*A61N 5/06* (2006.01)
*A61B 3/113* (2006.01)

(52) U.S. Cl.
CPC .............. *A61K 41/00* (2013.01); *A61B 3/113* (2013.01); *A61K 41/0023* (2013.01); *A61N 5/062* (2013.01); *C12N 13/00* (2013.01); *A61N 2005/0648* (2013.01)

(58) Field of Classification Search
None
See application file for complete search history.

(56) References Cited

U.S. PATENT DOCUMENTS

| | | | |
|---|---|---|---|
| 5,958,783 | A | 9/1999 | Josel et al. |
| 6,746,996 | B2 | 6/2004 | Reinhardt et al. |
| 2004/0023203 | A1 | 2/2004 | Miesenbock et al. |
| 2004/0122475 | A1 | 6/2004 | Myrick |
| 2009/0093403 | A1 | 4/2009 | Zhang et al. |
| 2010/0105120 | A1 | 4/2010 | Zebala |
| 2010/0178665 | A1 | 7/2010 | Ignatius et al. |

(Continued)

FOREIGN PATENT DOCUMENTS

| | | |
|---|---|---|
| CN | 102485731 | 6/2013 |
| EP | 3027229 | 6/2016 |

(Continued)

OTHER PUBLICATIONS

Rohan et al. ACS chemical Neurosci. (Feb. 18, 2013) 4: 585-593.*
Blazquez-Castro et al. Photochem. Photobiol. Sci. (2011) 10: 956-963.*
Machine translation of JP 2005312376 dowloaded from the JPO Jun. 23, 2007.*
Inaguma et al. Cancer (1999) 86(11): 2201-2211.*
Online abstract webpage for Numata et al. J. Am. Chem. Soc. (web online published Mar. 26, 2012) 134 (14): 6092-6095; down loaded from http://pubs.acs.org/doi/abs/10.1021/ja3007275?journalCode=jacsat&quickLinkVolume=134&quickLinkPage=6092&selectedTab=citation&volume=134 on Nov. 25, 2017 (Year: 2012).*
Online abstract for Numata et al. (J. Am. Chem. Soc. (2012; published on the web Mar. 26, 2012) 134: 6092-6095, downloaded from the American Chem society: pubs.acs.org/doi/abs/10.1021/ja3007275?journalCode=jacsat&quickLinkVolume=1; downloaded Nov. 25, 2017 (Year: 2012).*

(Continued)

*Primary Examiner* — Susan M Hanley
(74) *Attorney, Agent, or Firm* — BakerHostetler

(57) ABSTRACT

Methods and compositions modulate the activity of electrically excitable cells. Photovoltaic compounds which, upon exposure to light energy, increase or decrease the electrical activity of cells. These supplement and/or replace of vision based on the conversion of light energy to electrical energy within certain cells of the visual system. A "patch" or bridge to circumvent one or more defective, damaged, or diseased cells in the visual system. Additionally, in several embodiments, subjects with normal vision can benefit from the methods, compositions, systems, and/or devices disclosed herein as normal visual acuity can be heightened. The exposure induces an energy (e.g., a receipt of light energy, conversion to electrical energy, and passage of that electrical energy) from the photovoltaic compound to the cell, thereby altering the transmembrane potential of the cell and/or the opening of one or more ion channels, thereby modulating the activity of the electrically excitable cell.

10 Claims, 24 Drawing Sheets

(56) References Cited

U.S. PATENT DOCUMENTS

| | | | |
|---|---|---|---|
| 2010/0248299 A1* | 9/2010 | Lye | C12Q 1/04 435/34 |
| 2010/0267647 A1 | 10/2010 | Greenbaum et al. | |
| 2011/0217544 A1 | 9/2011 | Young et al. | |
| 2012/0034671 A1 | 2/2012 | Koder et al. | |
| 2012/0220922 A1 | 8/2012 | Yuste et al. | |
| 2012/0309045 A1 | 12/2012 | Knutson | |
| 2013/0309278 A1 | 11/2013 | Peyman | |
| 2014/0121260 A1 | 5/2014 | Nassar | |

FOREIGN PATENT DOCUMENTS

| | | |
|---|---|---|
| JP | 2005312376 A * | 11/2005 |
| JP | 2016-504930 | 2/2016 |
| WO | WO 2008/030548 A2 | 3/2008 |
| WO | WO 2008/116158 | 9/2008 |
| WO | 2011116238 | 9/2011 |
| WO | WO 2014/100283 | 6/2014 |
| WO | WO 2017/031380 | 2/2017 |

OTHER PUBLICATIONS

Watts et al. J. Am. Chem. Soc. (1971) 93(13): 3184-3188). (Year: 1971).*
He et al. (Inorganic Chem. (2012) 51: 4335-4352 (Year: 2012).*
Chen et al. Inorganic Chem. (1987) 26: 1116-1126 (Year: 1987).*
Zayat et al. J. Am. Chem. Soc. (2003) 125: 882-883 (Year: 2003).*
Abstract for Zayat et al. J. Am. Chem. Soc. (2003) 125: 882-883 downloaded from https://pubs.acs.org/doi/abs/10.1021/ja0278943 on Oct. 19, 2018 (Year: 2003).*
Zhang et al. Bioconjugate Chem. (2012) 23: 725-733 (Year: 2012).*
Dywer Nature (1957) 179: 425-426 (Year: 1957).*
Millet et al. Metal Ions in Biological Systems (1991), 27, 223-64 (Year: 1991).*
Rao et al. Proc. Natl. Acad. Sci. USA (1998) 95: 11526-11531 (Year: 1998).*
International Search Report and Written Opinion for PCT US/2013/076297, dated Apr. 25, 2014.
Search Report and Written Opinion received in PCT Application No. PCT/US16/47656, dated Oct. 31, 2016 in 18 pages.
De Araujo et al., "Ruthenium Phosphine/Diimine Complexes: Syntheses, Characterization, Reactivity with Carbon Monoxide, and Catalytic Hydrogenation of Ketones.", Organometallics, Mar. 13, 2005, vol. 24, No. 25 p. 6159-6168.
Numata, et al., "Utilization of Photoinduced Charge-Separated State of Donor-Acceptor-Linked Molecules for Regulation of Cell Membrane Potential and Ion Transport.", Journal of American Chemical Society, 2012, vol. 134, pp. 6092-6095.
Nazeeruddin, et al., "Synthesis, spectroscopic and a ZINDO study of cis-and trans-(X2)bis(4, 4'-dicarboxylic acid-2, 2'-bipyridine)ruthenium(II) complexes (X=Cl—, H20, NCS—)." Coordination Chemistry Reviews, 2000, vol. 2008, No. 1, pp. 213-225.
European Extended Search Report for EP 13865323.3 dated Jun. 20, 2017 in 6 pages.
Walther, et al., Photoinduced Process in Fluorene-Bridged Rhenium-Phenothiazine Dyads—Comparison of Electron Transfer Across Fluorene, Phenylene, and Xylene Bridges, 2010, Eur. J. Inor Chem . vol. 30, pp. 4843-4850.
Chen, et al., Intramolecular Electron Transfer in the Reductive Chromophere-Quencher Complex, Inorg. Chem., 1987, vol. 26, pp. 1116-1126.
Office Action for EP Application No. 13865323.3 dated Mar. 12, 2018.
Lu S. et al., "Cellular prostheses: functional abiotic nanosystems to probe, manipulate, and endow function in live cells", Nanomedicine: Nanotechnology, Biology and Medicine, Elsevier, NL, 2010, vol. 6, No. 3, pp. 409-418.
Notice of Allowance for U.S. Appl. No. 15/240,997 dated Mar. 12, 2018.
Aungst J. Pharmaceutical Sci. (1993) 82(101): 979-987.
Wilker, et al.; Chem. Int. Ed. 1999, "Substrates for Rapid Delivery of Electrons and Holes to Buried Active Sites in Proteins" 38, 90-92.
Dunn, A. et al.; Journal of American Chemical Society 2003, "Nanosecond Photoreduction of Cytochrome P450cam by Channel-Specific Ru-diamine Electron Tunneling Wires" 125, 12450-12456.

* cited by examiner

C

D

PHOTOACTIVATED MOLECULES FOR LIGHT-INDUCED MODULATION OF THE ACTIVITY OF ELECTRICALLY EXCITABLE CELLS AND METHODS OF USING SAME

RELATED CASES

This application is the U.S. National Phase under 35 U.S.C. § 371 of International Patent Application No. PCT/US2013/078297, filed on Dec. 18, 2013, which claims the benefit of U.S. Provisional Application No. 61/739,597, filed Dec. 19, 2012, U.S. Provisional Application No. 61/749,692, filed Jan. 7, 2013, U.S. Provisional Application No. 61/762,793, filed Feb. 8, 2013, U.S. Provisional Application No. 61/775,377, filed Mar. 8, 2013, and U.S. Provisional Application No. 61/905,056, filed Nov. 15, 2013, the entire disclosure of each of which is incorporated by reference herein in its entirety.

FEDERAL FUNDING

This inventon was made with government support under Grant No. EEC-0310723 awarded by the National Science Foundation and Grant Nos. GM85791, DK019038, and GM088967 awarded by the National Institutes of Health. The Federal Government has certain rights in the invention.

BACKGROUND

Field

The present application relates generally to compositions and methods for modulating the electrical activity of cells. In particular, the compositions and methods of their use allow for the light-induced activation of cells and/or modulation of the activity of cells through the exposure of the compositions to light energy.

Description of the Related Art

Degenerative diseases, in particular those involving loss of function of cells involved in vision affect a large number of people around the world and are the cause of loss of productivity, reduced quality of life and increased medical costs. While preventative therapies (such as cell therapy) are intended to slow, and in some cases reverse, degeneration, the timing of such therapies is critical, in that progression beyond a certain threshold may result in irrecoverable damage to tissues. Rescue (e.g., regenerative) therapies that restore function to otherwise partially or non-functional cells are desired, but as yet, generally unavailable.

SUMMARY

In several embodiments, there are provided methods, compositions, systems, and devices that allow supplementation and/or replacement of vision based on the conversion of light energy to electrical energy within certain cells of the visual system. In several embodiments, the methods, compositions, systems, and/or devices function as a "patch" or bridge to circumvent one or more defective, damaged, or diseased cells in the visual system. Additionally, in several embodiments, subjects with normal vision can benefit from the methods, compositions, systems, and/or devices disclosed herein as normal visual acuity can be heightened.

To these ends, in several embodiments, there is provided a method of modulating the activity of one or more electrically excitable cells comprising, placing a photovoltaic compound in close proximity and/or in contact with the electrically excitable cell or cells and exposing the photovoltaic compound to light energy. In several embodiments, the exposure induces an energy (e.g., a receipt of light energy, conversion to electrical energy, and passage of that electrical energy) from the photovoltaic compound to the cell, thereby altering the transmembrane potential of the cell and/or the opening of one or more ion channels, thereby modulating the activity of the electrically excitable cell. In several embodiments, an electron transfer is induced by exposure to light energy. In several embodiments, both energy and electron transfer is induced by exposure to light energy. In several embodiments, the alteration of the transmembrane potential is a depolarization that subsequently induces opening of one or more voltage sensitive ion channels, thereby resulting in an action potential in the cell (or series of action potentials). In several embodiments, one or more ion channels is opened by virtue of receiving, in close proximity, electrical energy from the photovoltaic compound (e.g., a large scale change in membrane potential may not be realized in circumstances where the compound is located close to a channel). In several embodiments, depending on the compound, the cell may be hyperpolarized. Advantageously, the compounds that are delivered can be targeted to over or underactive cells (or combinations) and thus allows tailored effects depending on the physiological state of the target cell or cells.

In several embodiments, the photovoltaic compound comprises a photovoltaic compound comprising a transition metal complex. In several embodiments, the transition metal complex comprises a transition metal (or metals) and at least one ligand. In several embodiments, the complex further comprises at least one hydrophobic molecule, which is optionally covalently attached to the at least one ligand.

In several embodiments, the ligand (or ligands) comprises a blue-emitting ligand, green-emitting ligand, a red-emitting ligand, or combinations thereof (when multiple ligands are used).

In several embodiments, the one ligand comprises a diimine ligand or isocyanide ligand. In several embodiments, the ligand is bipyridine.

Depending on the embodiment, the hydrophobic molecule is selected from an optionally substituted C1-C20 alkyl group, a C1-C20 alkenyl group, an optionally substituted C1-C20 alkynyl group, an optionally substituted C4-C10 cycloalkyl group, an optionally substituted C5-C10 aryl group, an optionally substituted C5-C10 heteroaryl group, and combinations thereof. In several embodiments, the hydrophobic molecule comprises a C17 alkyl group. In several embodiments, the at least one hydrophobic molecule serves to anchor the compound at the target electrically excitable cell.

In several embodiments, the transition metal within the complex is selected from the group consisting of iron, ruthenium, iridium, osmium, platinum, gold, rhenium, molybdenum, tungsten, platinum, rhodium, palladium, and combinations thereof. In several embodiments, a variety of transition metals are incorporated into complexes, which are then administered in combination (thereby capitalizing on the various light-reactive features of the various transition metals). In such a way, the photovoltaic compositions can be tailored for specific needs/output levels. In several embodiments, the transition metal is ruthenium. In additional embodiments, the transition metal is iridium.

In several embodiments, the photovoltaic compound comprises donor-bridge-acceptor complex, wherein the donor-bridge-acceptor complex comprises at least one donor molecule, at least one bridge, and at least one acceptor molecule.

In several embodiments, the donor molecule comprises one or more of phenothiazine, tetracene, and extended tetrathiafulvalene. In one embodiment, the donor molecule is phenothiazine.

In several embodiments, the at least one bridge has a length of about 2 nm. In several embodiments, the at least one bridge molecule ranges in length from about 0.5 nm to about 10 nm, including about 0.5 to about 1.0 nm, about 1.0 to about 1.5 nm, about 1.5 to about 2.0 nm, about 2.5 to about 3.0 nm, about 3.0 to about 3.5 nm, about 3.5 to about 4.0 nm, about 4.0 to about 6.0 nm, about 6.0 to about 8.0 nm, about 8.0 to about 10.0 nm, and overlapping ranges thereof. In several embodiments, the bridge length is customized to the electrical status of the cells in a recipient subject's eye. In some embodiments, longer or shorter bridges are used because the length of the bridge impacts the electrical energy transmitted to a recipient cell. In several embodiments, the at least one bridge comprises a highly π-conjugated system. In several embodiments, the at least one bridge comprises olioethynylenes, oligovinylenes, oligothiophenes, oligo(para-xylenes), oligo(meta-xylenes), oligo(para-dimethoxybenzene), oligo(meta-dimethoxy benzene), oligo(phenylene vinylenes), oligo(fluorenes), oligo(para-phenylenes), oligo(para-phenylene ethynylenes), and oligo(meta-phenylene ethynylenes).

In several embodiments, the at least one acceptor molecule comprises a transition metal complex (or complexes), wherein the transition metal complex comprises a transition metal and at least one ligand. In several embodiments, the transition metal complex has a transition metal selected from the group consisting of iron, ruthenium, iridium, osmium, platinum, gold, rhenium, molybdenum, tungsten, platinum, gold, rhodium, palladium, and combinations thereof. In several embodiments, combinations of transition metal complexes comprising various transition metals are used. In several embodiments, the transition metal is rhenium while in some embodiments, the transition metal is iridium. In several embodiments, the ligand (of the acceptor) is covalently attached to the at least one bridge. In one embodiment, the ligand comprises a diimine ligand or isocyanide ligand while in an additional embodiments, the ligand comprises 2,2'-bipyridine. In several embodiments, the acceptor transition metal complex is rhenium (I) tricarbonyl bipyridine pyridine, and the at least one bridge is covalently attached to the pyridine. In several embodiments, the transition metal complex comprises a metalloporphyrin. Various porphyrins may be used with various transition metals, depending on the embodiment. Porphyrins that can be used include, but are not limited to heme, protoporphyrin IX, protoporphyrinogen IX, coproporphyrinogen III, uroporphyrinogen III, hydroxymethyl bilane, porphobilinogen, δ-aminolevulinic acid, among others. In additional embodiments, metallocarroles are used, including, but not limited to aluminum and gallium corroles (or those with other metals). Additionally, in several embodiments, the metallocorroles are amphipathic, which advantageously aids in the incorporation of the molecule into a biological membrane. In still additional embodiments, various isocyanides may also be employed in order to effect charge separation and translation of light energy into electrical impulses. For example, tungsten, chromium, and/or molybdenum isocyanides may be used, depending on the embodiment. In several embodiments, it is preferred that the isocyanide metal complex is water soluble. In particular, one embodiment employs hexakis phenylisocyanide complexed with one (or more) of the group six transition metals. Such complexes can be derivatized with established methodologies.

In several embodiments light energy having a wavelength between about 300 and about 800 nm is used to stimulate the compound and thereby modulate the electrically excitable cell. In several embodiments, longer or shorter wavelengths are used, depending on the visual status of the subject, the conditions under which the compositions will be activated, and the like.

In several embodiments, the photovoltaic compositions are specifically targeted to one or more of a target tissue, a target cell population or a target region of a target cell (e.g., a region with high density of electrically-responsive channels). Targeting can be achieved, for example, by molecular (e.g., antibody-based, peptide-based, etc.) and/or physical (magnetic) targeting. Delivery is enhanced, in several embodiments, by packaging the compositions in a vesicle or other membrane bound structure, which can, in certain embodiments, be constructed with specific targeting mechanisms in mind.

Additionally, there is provided herein a system for generation of electrical activity in an electrically excitable cell, comprising a photovoltaic compound and a device configured to receive light energy and transmit the light energy to the photovoltaic compound. In several embodiments, the system is configured to generate electrical activity in an excitable cell in the eye of a subject. In several embodiments, the excitable cell targeted by the system is a retinal ganglion cell. Thus, in several embodiments, the photovoltaic compound is suitable for delivery to the eye of a subject, and in particular embodiments, the photovoltaic compound is suitable for delivery to the retinal ganglion cells of the subject.

In several embodiments, the prosthetic device of the system is configured to detect environmental light energy and amplify the light energy prior to transmitting the light energy to the photovoltaic compound. In several embodiments, the amplification allows vision in a subject having received the photovoltaic compound under normal conditions, or in some embodiments, under low-light conditions. In several embodiments, the prosthetic device is configured to detect a wide spectrum of environmental light energy and filter out one or more wavelengths of the light energy prior to transmitting the light energy to the photovoltaic compound. In several embodiments, this filtration allows a more refined transmission of energy to the photovoltaic composition and thus results in a more precise activation of the composition.

In several embodiments, the transmission of the light energy to the photovoltaic compound (whether filtered, amplified or otherwise processed) induces an intramolecular electron transfer and generation of a dipole across the photovoltaic compound, which in turn, induces the opening of one or more ion channels of the electrically excitable cell, thereby eliciting an action potential and generating electrical activity in an electrically excitable cell. In several embodiments, the transmission of the light energy to the photovoltaic compound induces the photovoltaic compound to accept an electron from a reductant compound, and wherein the electron acceptance induces membrane depolarization and/or the opening of one or more ion channels of the electrically excitable cell, thereby eliciting an action potential and generating electrical activity in an electrically excitable cell. In several embodiments, the recipient cell is a retinal ganglion cell and the generation of an action potential results in an electrical signal being sent along the optic nerve to the brain. In some embodiments, the photovoltaic composition allows generation of this action potential to the brain in circumstances where otherwise no such action potential would have been developed. Thus, as disclosed herein, the methods, compositions, systems and/or devices can function to restore or augment sight in a subject.

In several embodiments, the prosthetic device is configured to detect and movement of the eye of a subject wearing the device, such that the environmental light energy received by the device corresponds to the light energy at the position where the eyes of the subject were directed. Thus, in several embodiments, the device functions to respond to the eye position of the subject and provide information (e.g., in the form of light energy) that is processed by the chemistry and devices disclosed herein, to allow that subject to visualize objects and characteristics of the environment to which the subject's eyes were directed. In several embodiments, the prosthetic device is configured to preferentially direct light energy to the central visual field of the subject, and direct light energy less so to the peripheral regions of the subject's eye. In several embodiments, all, substantially all, or a significant portion of the subject's visual field is exposed to light energy. In several embodiments, the prosthetic device comprises glasses, goggles (or other external item) while in some embodiments, an internal prosthetic (e.g., an intraocular camera) is employed. In several embodiments, the prosthetic device processes the light energy (e.g., the images) and directs it output to specific layer or region of the retina (e.g., the output signal is processed such that it "matches" the signal type that a specific retinal cell may normally receive, as the output from the prosthetic device is being input into the visual pathway mid-stream). The processing can include various alterations to the images (e.g., filtration of wavelength, edge detection enhancement, changes intensity, etc.).

In several embodiments, the modulation of the activity of the electrically excitable cell is used to replace the function of diseased electrically excitable cells. In several embodiments, the methods are used to modulate retinal ganglion and/or photoreceptor cells. In several such embodiments, the methods and compositions are used to treat blindness.

The methods summarized above and set forth in further detail below describe certain actions taken by a practitioner; however, it should be understood that they can also include the instruction of those actions by another party. Thus, actions such as "administering a photovoltaic nanoswitch" include "instructing the administration of a photovoltaic nanoswitch."

BRIEF DESCRIPTION OF THE DRAWINGS

FIG. 1A depicts the normalized absorption, excitation, and uncorrected emission spectra of RubpyC17. FIG. 1B depicts the chemical structure of RubpyC17, where n=16. FIG. 1C depicts images obtained of INS (top row), HEK293T (middle row) and chromaffin (bottom row) cells under brightfield illumination (left column), before addition of RubpyC17 (middle column) and immediately after addition of 10 µM RubpyC17 (right column). Luminescent images (right column) were obtained by collecting emitted light using a red filter set following excitation with 488 nm light from an Argon Ion laser. FIG. 1D is a schematic diagram depicting the predicted light-induced electron flow. Light illumination places RubpyC17 in an unstable excited state such that it prefers to donate or accept electrons. If an electron donor (reductant, represented as D in figure) is present, RubpyC17 molecules will accumulate electrons creating a negative field potential just outside the cell membrane, which is observed by the cell as a depolarization. This depolarization is sufficient to induce opening of voltage-gated ion channels.

FIG. 1A shows a summary bar graph showing averaged depolarization and hyperpolarization values of RubpyC17-loaded INS and HEK293T cells when stimulated by blue light illumination. FIGS. 2B-2G are representative traces from cells depicted in A. FIG. 2B shows the membrane potential recording from an INS cell that was not exposed to RubpyC17 in the presence of 2 mM ascorbate (AA) showed no changes during light stimulation (bar). FIG. 2C shows a membrane potential recording from an INS cell that was transiently exposed to RubpyC17 for 2 min in the presence of 2 mM ascorbate (AA) depolarized during light stimulation (bar). FIG. 2D shows a membrane potential recording from an INS cell that was transiently exposed to RubpyC17 for 2 min in standard extracellular solution without supplementation of reductants or oxidants still showed light-induced depolarization. FIG. 2E shows a membrane potential recording from an HEK293T cell that was transiently exposed to RubpyC17 for 2 min in the presence of 2 mM ascorbate (AA) depolarized during light stimulation (bar). FIG. 2F shows a Membrane potential recording from an HEK293T cell that was transiently exposed to RubpyC17 for 2 min in the presence of an alternate reductant, 0.1 mM ferrocyanide (ferrO) depolarized during light stimulation (bar). FIG. 2G shows a membrane potential recording from an HEK293T cell that was transiently exposed to RubpyC17 for 2 min in the presence of an oxidant, 0.1 mM ferricyanide (ferrI) hyperpolarized during light stimulation (bar).

FIG. 3A demonstrates that in the presence of 5 mM ascorbate, blue light illumination increased the rate of action potential firing by chromaffin cells incubated in 900 nM RubpyC17 for 30 min. FIG. 3B demonstrates that in the presence of 0.1 mM ferricyanide, blue light illumination decreased the rate of action potential firing by chromaffin cells incubated in 450 nM RubpyC17 for 30 min. FIG. 3C shows that there were no obvious changes in action potential waveforms of RubpyC17-treated cells before and during light illumination. FIG. 3D shows a bar graph depicting the percent increase relative to control (dark) of action potential firing rate during light illumination, in chromaffin cells treated with RubpyC17 in the presence of 5 mM ascorbate (n=12) and 0.1 mM ferricyanide (n=8). FIG. 3E shows that blue light illumination increased the rate of action potential firing by a RubpyC17-loaded chromaffin cell (2 µM, 1.5 min) during perfusion of 5 mM ascorbate but decreased the rate of action potential firing by during perfusion of 0.2 mM ferricyanide. Bar in all traces indicates the duration of blue light illumination.

FIG. 4A shows data related to mouse chromaffin cells that were pre-incubated with 2 µM RubpyC17 for 1.5 min in a modified extracellular solution containing 20 mM KCl, catecholamine secretion was monitored and detected using carbon fiber amperometry before, during (bar) and after blue light illumination. FIG. 4B depicts the secretion pattern of a control mouse chromaffin cell that was not exposed to RubpyC17. FIG. 4C depicts examples of individual amperometric spikes elicited by light illumination in chromaffin cells treated with 2 µM RubpyC17. Scale bars=5 ms, 0.1 nA. FIG. 4D depicts a bar graph measuring the percent increase relative to control (dark) of secretion spikes during light illumination in control chromaffin cells (not treated with RubpyC17) (n=8) and RubpyC17-treated chromaffin cells (n=18).

FIGS. 5A-5B depict membrane current monitored in voltage-clamp mode showed that light illumination did not trigger current changes in RubpyC17-loaded INS cells. Inset images shown to the right of trace confirmed proper integration of RubpyC17 in patched cells. FIGS. 5C-5E show the light-induced action potential firing in chromaffin cells was not due to biophysical changes in voltage-gated ion channels as there were no significant changes in current-voltage relationships (C-D) nor in steady-state activation curve (E) in RubpyC17-loaded chromaffin cells before (open circle) or during (open circle) light illumination. Specifically, FIG. 5C shows a current-voltage relationship that was obtained in voltage-clamp mode using a resting potential of −80 mV and depolarizing the cell in 10 mV increments, from −70 mV to 100 mV, before and during light-illumination. Peak inward currents from each stimulation jump were plotted against corresponding stimulating voltages (n=6). FIG. 5D shows a current-voltage relationship that was obtained in voltage-clamp mode using a resting potential of −80 mV and stimulating the cell with a ramping depolarization ranging from −100 mV to +60 mV, before and during light illumination. Data from representative cell is shown (n=5). FIG. 5E shows a steady-state activation curve that was generated by measuring the peak tail current immediately following a short 0.5 ms depolarizing jumps to −70 to +100 mV from a resting potential of −80 mV (n=5). FIG. 5F demonstrates that inclusion of 18 µM of RubpyC17 (top trace) in the intracellular solution inside the patch pipette did not perforate chromaffin cells (n=10), unlike inclusion of amphoterecin B (bottom trace, n=4). Currents resulting from capacitor-like behavior of chromaffin cell membranes during hyperpolarizing jumps to −85 mV from a resting membrane potential of −80 mV were recorded 5 min following giga-seal formation for amphoterecin B (bottom trace) or 10 min following giga-seal formation for RubpyC17 (top trace). FIG. 5G shows that substitution of sodium ions by NMDG and potassium by cesium, dramatically reduced both inward and outward current in INS cells. FIG. 5H shows that in external solution where NMDG was substituted for sodium ions, and cesium for potassium ions, RubpyC17-loaded INS cells still underwent light-induced depolarization in the presence of ascorbate (n=5, NMDG solution, n=14, standard solution, n=6, control cells not exposed to RubpyC17).

FIG. 15A shows data from wild type rats. FIG. 15B shows RCE rats injected with vehicle. FIGS. 15C-15F depict data related to administration of Rubpy-C17. White light was used for illumination in panels A, C, and D, while blue light (450 nm) was used in panels B, E, and F.

DETAILED DESCRIPTION

Figures 1A, 1B, 1C:
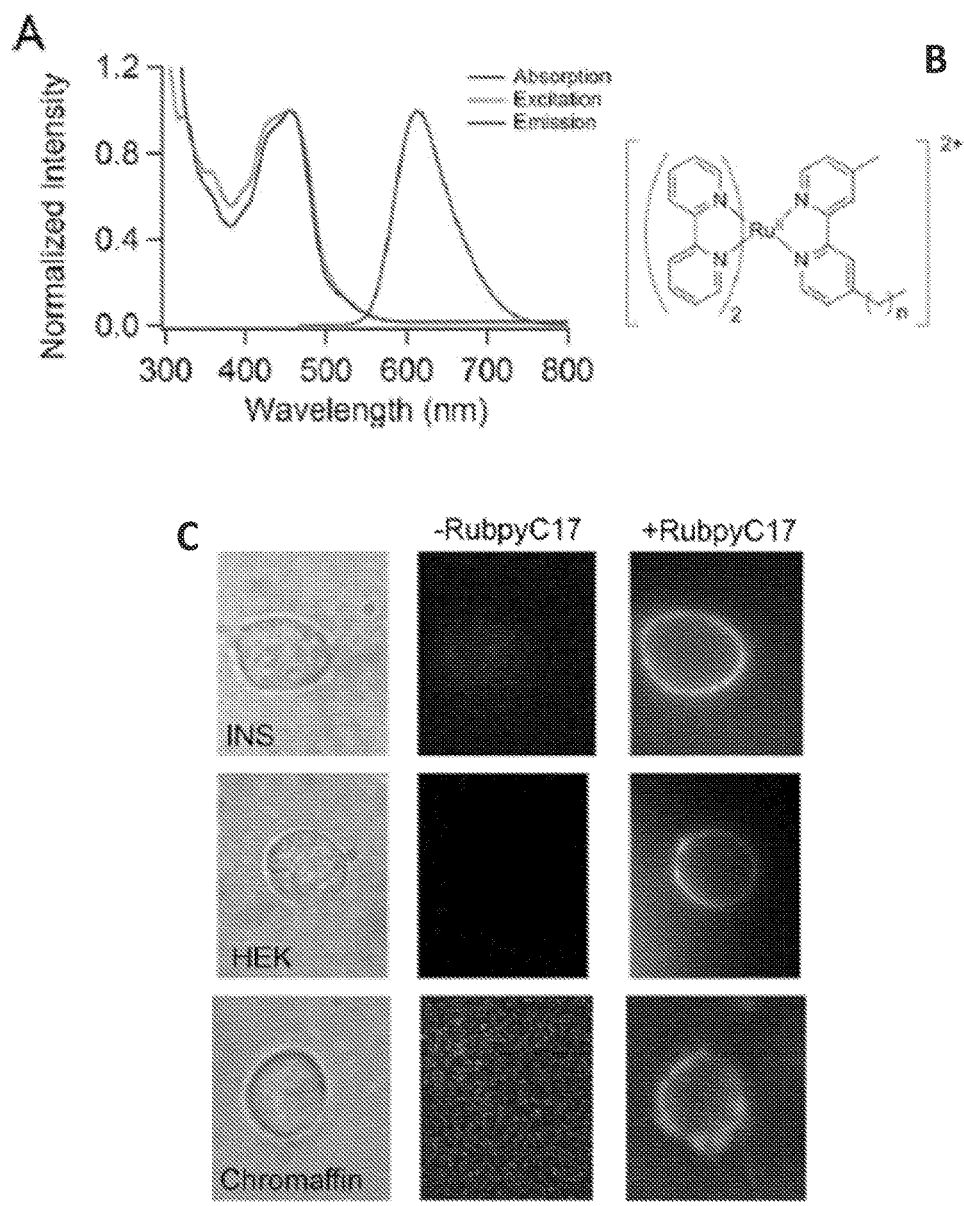
FIGS. 1A-1D depict incorporation of RubpyC17 in plasma membranes of live cells.

The loss of neuronal activity is the cause of myriad of health problems and diseases that cause reduction in quality of life, possible loss of ability to work and, increased medical costs and familial burdens due to patient care. Many therapies seek to prevent and/or reduce the progression of diseases involving reduced neuronal activity, but often, there is little chance to restore function once it is lost. Moreover, once functionality is reduced beyond a certain threshold, degeneration may continue to build until substantially all function is lost. After a period of substantially reduced function or non-functionality, many excitable tissues undergo a rough corollary to muscular atrophy (e.g., if you don't use it, you lose it). However, recent discoveries have indicated that certain excitable tissues can recover function, at least to some degree, even after periods of substantial inactivity.

In ocular diseases, the degeneration of the retina, due to one or more of many causes, leads to the dysfunction and eventual cell death of photoreceptors, the functional heavyweight of the vision system. In brief, photoreceptors function via the generation of a biochemical cascade after a light stimulus (via the photopigment rhodopsin), which in turn results in electrophysiological stimulation of retinal neurons. In the absence of properly functioning photoreceptors, this "light to chemical to electrical" cascade is compromised, and with continual degeneration, blindness is the nearly inevitable result. To address this ongoing concern with loss of vision, there exists a need to be able to stimulate retinal neurons, in the absence of a full complement of normally functioning photoreceptors.

In several embodiments disclosed herein, various optically active complexes are disclosed that allow the transmission of light energy to a retinal neurons, even in the absence of functioning photoreceptors. Optical approaches to control cellular activity, particularly neuronal activity, are gaining attention as possible therapeutic modalities. In some instances, attempts have been made to control cellular membrane potential by heterologously expressing light-responsive proteins in cell, thereby rendering them light-sensitive (e.g., cloning of natural, but non-mammalian light-sensitive transporters such as channelrhodopsins and halorhodopsins). Another light-sensitive class of proteins that has also been cloned and expressed heterologously is melanopsin, a photoisomerizable pigment that signals through the G protein of the $G_q$ family in a specialized subset of retinal ganglion cells.

Alternative approaches have employed synthetic chemistry to generate photolabile "caged" neurotransmitters that liberate the neurotransmitter upon photolysis by UV illumination, thereby enabling light to activate ligand-gated ion channels. Another synthetic chemistry approach involves use of small diffusible "photoswitch" compounds that act directly on native ion channels to induce light-triggered changes in membrane potential (e.g., the photoisomerization of azobenzene). When covalently attached to one or two potassium channel blocker moieties (tetraethylammonium), azobenzene compounds are internalized by cells and interact with potassium channels to either block or unblock outward potassium flux, when alternating illumination wavelengths between 500 and 380 nm. Azobenzene compounds have also been covalently attached to ion channels at cysteine residues, introduced by site-directed mutagenesis, to enable activation or block of either voltage-gated or ligand-gated ion channels. However, the blockage or unblockage of potassium flux (and hence the activity or inactivity of the cell) is tied to the repeated stimulation of the compound by UV light.

Thus, while such approaches may show some modulation of cellular electrical activity and offer useful tools for basic research, these approaches require either heterologous expression of high levels of foreign proteins and/or excitation by ultraviolet illumination. These requirements present possible immune issues in subjects, present risk of adverse side effects from the stimulation source, and are therefore would severely limited in their translation to clinical applications. The compounds and method disclosed herein, in contrast, allow the translation of light energy to cellular electrical activity without the requirements of expression of high levels of foreign proteins or excitation by ultraviolet illumination. Thus, several embodiments disclosed herein are readily applicable to clinical contexts, in which they unexpectedly serve to restore (albeit synthetically) function to the eye, and sight to a patient who would otherwise be largely or completely blind.

Photovoltaic Nanoswitches

Recently, new approaches involving a new class of synthetic photoswitches that generate charge separation upon illumination at visible wavelengths have been under investigation. Ferrocene-porphyrin-C60 compounds targeted to cell membranes using cell-penetrating, high-density lipoprotein, induce a light-dependent membrane depolarization, though the mechanisms are not yet thoroughly understood. However, a key limitation of the ferrocene-porphyrin-C60 compounds is that their action is confined to inhibiting potassium channels, and hence they can only depolarize the cell.

Several embodiments described herein related to another class of synthetic photovoltaic nanoswitches that respond to light of visible wavelengths by creating an electrical dipole sufficient to alter cell membrane potential. In other words, these compositions are suitable for separating charge to a sufficient degree to induce either (i) activation of one or more voltage-sensitive ion channels, which leads to depolarization or hyperpolarization of the cell (depending on the embodiment) or (ii) inducing a localized change in membrane potential such that an action potential is triggered.

As discussed in more detail below, ruthenium diimine complexes (or other complexes incorporating other transition metals and/or other organic ligands) are used to facilitate light-activated electron transfer to an excitable cell (or cells, depending on the embodiment). For example, excitation at 488 nm (or other visible wavelengths) leads to a photoexcited state, in which the complex can either accept or donate an electron in the presence of a soluble sacrificial reductant or oxidant, respectively. In several embodiments, these complexes are employed in mediating light-induced changes in cellular electrical activity. For example, $[Ru(bpy)_2(bpy\text{-}C17)]^{2+}$ (where bpy is 2,2'-bipyridine and bpy-C17 is 2,2'-4-heptadecyl-4'-methyl-bipyridine) readily incorporates into the plasma membrane of cells, as evidenced by membrane-confined luminescence. Excitable cells incubated in $[Ru(bpy)_2(bpy\text{-}C17)]^{2+}$ and then illuminated at 488 nm in the presence of the reductant ascorbate (or other reductants, depending on the embodiment) undergo membrane depolarization leading to firing of action potentials. In contrast, the same experiment performed with the oxidant ferricyanide, instead of ascorbate, leads to hyperpolarization.

It shall be appreciated that other oxidants or reductants are involved in other embodiments, particularly those in an in vivo setting. Typical reductants include, but are not limited to, sodium dithionite and titanium citrate. Typical oxidants include, but are not limited to, hydrogen peroxide ($H_2O_2$), hydroxyl radical, nitric oxide (NO), peroxynitrite, and nitrogen dioxide, among others.

Other transition metals may also be used, depending on the embodiment. For example, in several embodiments metals with atomic number greater than 40 are used. In several embodiments, preferred metals are iron, ruthenium, iridium, osmium, platinum, gold, rhenium, molybdenum, tungsten, platinum, gold, rhodium, and palladium. For example, in several embodiments, thermally stable d6 metals are used, including but not limited to Fe(II), Ru(II), Os(II), Ir(III), Re(I), Mo(0), and W(0). In some embodiments, d8 complexes, such as Pt(II) and Ir(I), are used. In some embodiments, the transition metal is ruthenium. In some embodiments, the transition metal is iridium, which, depending on the embodiment may be more chemically stable and/or less potentially toxic than rhenium. Combinations of metals may also be used (e.g., a mixture of photovoltaic nanoswitches, each having a different transition metal). Use of various transition metals allow, depending on the embodiment, a tunable range of light absorption ranging from between about 375 and about 800 nm. Experiments (discussed in greater detail below) confirm that illumination of membrane-associated $[Ru(bpy)_2(bpy\text{-}C17)]^{2+}$ in the presence of ascorbate alters the cell membrane potential by increasing the negative charge on the outer face of the cell membrane capacitor—effectively depolarizing the cell membrane (and vice versa for ferricyanide).

It shall also be appreciated that other ligands are used in still additional embodiments. By selecting various ligands (or combinations thereof), one can achieve a tunable range of light absorption ranging from between about 375 and about 800 nm. Furthermore, the ligands may be the same or different in a transition metal complex. Depending on the embodiments, the ligand is a blue-emitting ligand, a green-emitting ligand, or a red-emitting ligand.

In several embodiments, the emission from transition metal complexes is controlled by ligand modifications. For example, in several embodiments, addition of electronegative atoms, such as, for example, fluorine, induces a hypsochromic shift in the emission spectrum. Alternatively, the addition of electron-donating substituents to a ligand increases emission energy and correspondingly shortens emission wavelengths. Combinations of various ligand modifications are also used, in several embodiments, in order to tune the emission spectra to a desired range. See also, Thompson et al., "Organometallic Complexes for Optoelectronic Applications" in Comprehensive Organometallic Chemistry III (2007), herein incorporated by reference in its entirety.

In several embodiments, the ligand comprises a diimine ligand and/or isocyanide ligand. Typical ligands include but are not limited to 2,2'-bipyridine (bpy), 4,4'-dimethyl-2,2'-bipyridine ($Me_2bpy$), 2,2'-bipyrimidine (bpm), 2,2'-biisoquinoline (biiq), 1,10-phenanthroline (phen), dipyrido[3,2-c:2',3'-e]pyridazine (taphen), 2,2'-biquinoline (biq), 6,7-dihydrodipyrido[2,3-b:3,2-j][1,10]-phenanthroline (dinapy), 2-(2[pyridyl]quinoline (pq), 1-(2-pyrimidyl)pyrazole] (pzpm), 2,2'-biimidazole ($H_2biim$), 4,4'-di-tert-butyl-2,2'-dipyridyl (dtb-bpy), 4,4'-methoxy-2,2'-dipyridyl (MeO-bpy), 4,4'-dimethyl-2,2'-bipyridine (dmb), bipyrazine, bipyridazine, azo-bipyridine, aryl isocyanides, alkyl isocyanides (such as methyl isocyanide or t-butyl isocyanide, and benzyl isocyanide.

In several embodiments, at least one ligand is covalently attached (or otherwise chemically associated with) to at least one hydrophobic molecule that serves to anchor the transition metal complex at the target electrically excitable cell. In several embodiments, more than one hydrophobic molecule is attached to a ligand, and, optionally more than one ligand is attached to a hydrophobic molecule. Non-limiting examples of hydrophobic molecules include optionally substituted $C_1$-$C_{20}$ alkyl groups, $C_1$-$C_{20}$ alkenyl groups, optionally substituted $C_1$-$C_{20}$ alkynyl groups, optionally substituted $C_4$-$C_{10}$ cycloalkyl groups, optionally substituted $C_4$-$C_{10}$ aryl groups, and optionally substituted $C_4$-$C_{10}$ heteroaryl groups. For example, the 17-carbon aliphatic chain (C17) covalently attached to one of the three bipyridine (bpy) ligands in RubpyC17 serves to anchor the compound in the cellular plasma membrane.

As discussed in more detail below, patch clamp experiments were performed to further elucidate the mechanisms involved. Namely, two alternative explanations for light-induced membrane potential changes were dismissed: (1) light-induced direct interaction of $[Ru(bpy)_2(bpy-C17)]^{2+}$ with ion channels, and (2) light-induced membrane perforation. Further, the experiments disclosed herein indicate that incorporation of $[Ru(bpy)_2(bpy-C17)]^{2+}$ into the plasma membrane of neuroendocrine cells enables light-induced secretion as monitored by amperometry. It shall be appreciated that while the present work employs a ruthenium diimine complex as an example, these data point more generally to broader application of transition metal complexes to mediate light-induced biological changes.

More specifically, ruthenium-diimine complexes and their capacity for light-activated electron transfer have been studied in redox metalloproteins. They are excited at the blue end of the visible electromagnetic spectrum and luminesce in the red. The compound described here is $[Ru(bpy)_2(bpy-C17)]^{2+}$ where bpy is 2,2'-bipyridine and bpy-C17 is 4-heptadecyl-4'-methyl-2,2'-bipyridine, which will be referred to from now on as RubpyC17. Illumination generates a photoexcited compound that can either accept or donate an electron by intermolecular transfer, depending on whether a sacrificial reductant (e.g. ascorbate) or oxidant (e.g. ferricyanide) is present. Of course, other sacrificial reductants or sacrificial oxidants may be employed, depending on the embodiment. The addition of a 17-carbon aliphatic chain (C17) to one of the three bipyridine (bpy) ligands in RubpyC17 serves to anchor the compound in the cellular plasma membrane. In other words, a fatty acid "tail" functions to anchor the photoexcitable compound in the lipid bilayer of cells. It shall be appreciated that other aliphatic chain lengths may also be employed, depending on the embodiment, including but not limited to C5, C8, C10, C12, C15, C18, C20, C24 and CX (wherein X is a desired number of carbons) aliphatic chains (and lengths overlapping with the above-referenced lengths). Light-activated electron transfer at this membrane-anchored compound alters the charge of the cell membrane capacitor, inducing either a depolarization in the presence of excess reductants or hyperpolarization in the presence of excess oxidants. Further, this light-induced change in membrane potential is sufficient to open and close voltage-gated ion channels such that action potential firing rate (and secretion) can be regulated and manipulated in neuroendocrine cells (or other electrically excitable cells, such as, for example, retinal ganglion cells) by light.

Donor-Bridge Acceptor Molecules

As an alternative to photovoltaic nanoswitches, as disclosed herein, donor-bridge-acceptor compositions are used in several embodiments as synthetic molecules that allow for charge separation along the length of the composition upon exposure to light. In several embodiments, such molecules are tunable with respect to not only their absorption of light energy, but also the "lifetime" of their activation, based (at least in part) on the size of the bridge portion of the molecule.

By way of background, photoinduced long-range electron transfer (ET) plays a key role in artificial photosynthesis, and optoelectronic devices. Critical to all of these systems is the precise control of ET rates over long distances. ET has been shown to be influenced by many factors, including the electron tunneling distance, donor-acceptor energetics, and the chemical structure of the bridge. Among these parameters, the chemical structure of the bridge plays a key role; even small changes in its chemical structure have been shown to affect the rate of ET.

Donor-bridge-Acceptor (D-B-A) complexes allow systematic investigation of parameters that control these ET processes. Previous studies of ET in D-B-A complexes showed that highly π-conjugated systems such as oligo (phenylene vinylenes), oligo(fluorenes), oligo(para-phenylenes), and oligo(para-phenylene ethynylenes) are attractive mediators of long-range ET. Specifically, π-conjugated oligomeric systems provide efficient electronic coupling between electron donor and acceptor and display wire-like behavior. Systems with para connections exhibit a linear configuration that may be useful for spanning a cellular membrane. Also, π-conjugated oligomeric systems exhibit rapid forward electron transfer; however, many are hindered by equally fast charge recombination (e.g., return of the electron to its original position and energy state), which limits their efficiency in practical applications. Thus, in several embodiments, oligo(meta-phenylene ethynylenes)

are used as bridges since these systems have relative flexibility and may favor efficient forward ET over charge recombination.

In several embodiments disclosed herein, a donor-bridge-acceptor complex comprises at least one donor molecule, at least one bridge, and at least one acceptor molecule. The donor molecule (or molecules), depending on the embodiment include, but are not limited to, phenothiazine, tetracene, extended tetrathiafulvalene, and combinations thereof. For example, phenothiazine (PTZ) was used as electron donor in several of the non-limiting experiments described below.

The bridge of the donor-bridge-acceptor complex may be bridges known in the art. For example, optionally substituted $C_{10}$-$C_{20}$ alkyl chains may be used as a bridge. In several embodiments, the at least one bridge is a highly π-conjugated system. The bridge can be typical bridge molecules used in D-B-A complexes. Non-limiting examples include olioethynylenes, oligovinylenes, oligothiophenes, oligo (para-xylenes), oligo(meta-xylenes), oligo(para-dimethoxybenzene), oligo(meta-dimethoxy benzene), oligo(phenylene vinylenes), oligo(fluorenes), oligo(para-phenylenes), oligo (para-phenylene ethynylenes), and oligo(meta-phenylene ethynylenes).

In several embodiments, the bridge has a length of about 5 nm to about 1 nm. In several embodiments, the bridge has a length of at least about 4 nm, at least about 3 nm, at least about 2 nm, or at least about 1 nm. In several embodiments, the bridge has a length of about 2 nm. Other lengths of bridges (or compositions comprising compounds with various length bridges are also used, in several embodiments, in order to increase the responsiveness and range of the compounds reactivity to light, and to account for the various types of electrically excitable cells that may require stimulation in a given embodiment.

Transition metal complexes are advantageous for use as acceptors in certain embodiments of D-B-A molecules, as they are able to act as potent excited-state oxidants or reductants and possess longer excited-state lifetimes compared to similar organic D-B-A systems. For example, rhenium(I) tricarbonyl bipyridine pyridine was chosen as an electron acceptor in several of the non-limiting experiments described below.

In several embodiments, the acceptor molecule comprises a transition metal complex, having a transition metal and at least one ligand. In several embodiments, the transition metal is selected from the group consisting of iron, ruthenium, iridium, osmium, platinum, gold, rhenium, molybdenum, tungsten, platinum, gold, rhodium, and palladium. In some embodiments, the transition metal is iridium, which, depending on the embodiment may be more chemically stable and/or less potentially toxic than rhenium. Combinations of metals may also be used (e.g., a mixture of photovoltaic nanoswitches, each having a different transition metal). In several embodiments, the transition metal complex comprises a metalloporphyrin. Various porphyrins may be used with various transition metals, depending on the embodiment. Porphyrins that can be used include, but are not limited to heme, protoporphyrin IX, protoporphyrinogen IX, coproporphyrinogen III, uroporphyrinogen III, hydroxymethyl bilane, porphobilinogen, δ-aminolevulinic acid, among others. In additional embodiments, metallocarroles are used, including, but not limited to aluminum and gallium corroles (or those with other metals). Additionally, in several embodiments, the metallocorroles are amphipathic, which advantageously aids in the incorporation of the molecule into a biological membrane. In still additional embodiments, various isocyanides may also be employed in order to effect charge separation and translation of light energy into electrical impulses. For example, tungsten, chromium, and/or molybdenum isocyanides may be used, depending on the embodiment. In several embodiments, it is preferred that the isocyanide metal complex is water soluble. In particular, one embodiment employs hexakis phenylisocyanide complexed with one (or more) of the group six transition metals. Such complexes can be derivatized with established methodologies.

In several embodiments wherein a transition metal complex comprises the acceptor, at least one ligand of the transition metal complex is covalently attached (or otherwise chemically associated with) to at least one bridge. More than one bridge may be attached to a ligand, and optionally, more than one ligand may be attached to a bridge. Depending on the embodiment, the ligands may be the same or different in a given transition metal complex. As described above, varying the ligand and/or modifying the ligand allow a tunable range of light absorption ranging from between about 375 and about 800 nm (or shorter or longer wavelengths, depending on the embodiment). For example, in one embodiment, the ligand comprises a diimine ligand. In additional embodiments, the ligand comprises an isocyanide ligand. Additional ligands include, but are not limited, to 2,2'-bipyridine (bpy), 4,4'-dimethyl-2,2'-bipyridine (Me₂bpy), 2,2'-bipyrimidine (bpm), 2,2'-biisoquinoline (biiq), 1,10-phenanthroline (phen), dipyrido[3,2-c:2',3'-e]pyridazine (taphen), 2,2'-biquinoline (biq), 6,7-dihydrodipyrido[2,3-b:3,2-j][1,10]-phenanthroline (dinapy), 2-(2[pyridyl)quinoline (pq), 1-(2-pyrimidyl)pyrazole] (pzpm), 2,2'-biimidazole (H₂biim), 4,4'-di-tert-butyl-2,2'-dipyridyl (dtb-bpy), 4,4'-methoxy-2,2'-dipyridyl (MeO-bpy), 4,4'-dimethyl-2,2'-bipyridine (dmb), bipyrazine, bipyridazine, and azo-bipyridine.

Disclosed herein are also the schemes for the synthesis and photophysical properties of a D-B-A complex based on a transition metal derivative, rhenium tricarbonyl pyridine diimine, linked via an oligo(meta-phenylene ethynylene) bridge to phenothiazine (PTZ).

While certain of the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

As used herein, "$C_a$ to $C_b$" or "$C_{a-b}$" in which "a" and "b" are integers shall be given its ordinary, scientifically recognized meaning and shall also refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

As used herein, "alkyl" shall be given its ordinary meaning and shall also refer to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although this definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, e.g., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkenyl" shall be given its ordinary meaning and shall also refer to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" shall be given its ordinary meaning and shall also refer to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, Butyn-4-yl, and 2-butynyl. Typical alkynyl groups include, but are in no way limited to, ethynyl, propynyl, butynyl, pentynyl, and hexynyl, and the like.

As used herein, "heteroalkyl" shall be given its ordinary meaning and shall also refer to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_1$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "cycloalkyl" shall be given its ordinary meaning and shall also mean a fully saturated carbocyclyl ring or ring system. Non-limiting examples include cyclopropyl, cyclobutyl, cyclopentyl, and cyclohexyl.

As used herein, "aryl" shall be given its ordinary meaning and shall also refer to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "heteroaryl" shall be given its ordinary meaning and shall also refer to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl As used herein, "carbocyclyl" shall be given its ordinary meaning and shall also refer a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl.

As used herein, "heterocyclyl" shall be given its ordinary meaning and shall also refer to a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

The term "(heterocyclyl)alkyl" shall be given its ordinary meaning and shall also refer to a heterocyclyl group connected, as a substituent, via an alkylene group. Examples include, but are not limited to, imidazolinylmethyl and indolinylethyl.

The term "halogen" or "halo," as used herein, shall be given its ordinary meaning and shall also mean any one of the radio-stable atoms of column 7 of the Periodic Table of the Elements, e.g., fluorine, chlorine, bromine, or iodine, with fluorine and chlorine being preferred, in certain embodiments.

As used herein, "alkoxy" shall be given its ordinary meaning and shall also refer to the formula —OR wherein R is an alkyl as is defined above, such as "C1-9 alkoxy", including but not limited to methoxy, ethoxy, n-propoxy, 1-methylethoxy (isopropoxy), n-butoxy, iso-butoxy, sec-butoxy, and tert-butoxy, and the like.

A "cyano" group, as used herein, shall be given its ordinary meaning and shall also refer to a "—CN" group.

As used herein, the terms "aryloxy" and "arylthio" shall be given their ordinary meanings and shall also refer to RO— and RS—, in which R is an aryl as is defined above, such as "C6-10 aryloxy" or "C6-10 arylthio" and the like, including but not limited to phenyloxy.

As used herein, an "amino" group shall be given its ordinary meaning and shall also refer to a "—NRARB" group in which RA and RB are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein. A non-limiting example includes free amino (i.e., —NH2).

As used herein the term "cyanato" group shall be given its ordinary meaning and shall also refer to an "—OCN" group.

As used herein, the term "isocyanato" group shall be given its ordinary meaning and shall also refer to a "—NCO" group.

As used herein the term "thiocyanato" group shall be given its ordinary meaning and shall also refer to a "—SCN" group.

As used herein, the term "isothiocyanato" group shall be given its ordinary meaning and shall also refer to an "—NCS" group.

As used herein, the term "sulfinyl" group shall be given its ordinary meaning and shall also refer to an "—S(=O)R" group in which R is selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, the term "sulfonyl" group shall be given its ordinary meaning and shall also refer to an "—SO2R" group in which R is selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, the term "substituted group" shall be given its ordinary meaning and shall also refer to groups derived from the unsubstituted parent group in which there has been an exchange of one or more hydrogen atoms for another atom or group. Unless otherwise indicated, when a group is deemed to be "substituted," it is meant that the group is substituted with one or more substituents independently selected from C1-C6 alkyl, C1-C6 alkenyl, C1-C6 alkynyl, C1-C6 heteroalkyl, C3-C7 carbocyclyl (optionally substituted with halo, C1-C6 alkyl, C1-C6 alkoxy, C1-C6 haloalkyl, and C1-C6 haloalkoxy), C3-C7-carbocyclyl-C1-C6-alkyl (optionally substituted with halo, C1-C6 alkyl, C1-C6 alkoxy, C1-C6 haloalkyl, and C1-C6 haloalkoxy), 5-10 membered heterocyclyl (optionally substituted with halo, C1-C6 alkyl, C1-C6 alkoxy, C1-C6 haloalkyl, and C1-C6 haloalkoxy), 5-10 membered heterocyclyl-C1-C6-alkyl (optionally substituted with halo, C1-C6 alkyl, C1-C6 alkoxy, C1-C6 haloalkyl, and C1-C6 haloalkoxy), aryl (optionally substituted with halo, C1-C6 alkyl, C1-C6 alkoxy, C1-C6 haloalkyl, and C1-C6 haloalkoxy), aryl(C1-C6)alkyl (optionally substituted with halo, C1-C6 alkyl, C1-C6 alkoxy, C1-C6 haloalkyl, and C1-C6 haloalkoxy), 5-10 membered heteroaryl (optionally substituted with halo, C1-C6 alkyl, C1-C6 alkoxy, C1-C6 haloalkyl, and C1-C6 haloalkoxy), 5-10 membered heteroaryl(C1-C6)alkyl (optionally substituted with halo, C1-C6 alkyl, C1-C6 alkoxy, C1-C6 haloalkyl, and C1-C6 haloalkoxy), halo, cyano, hydroxy, C1-C6 alkoxy, C1-C6 alkoxy(C1-C6)alkyl (i.e., ether), aryloxy, sulfhydryl (mercapto), halo(C1-C6)alkyl (e.g., —CF3), halo(C1-C6)alkoxy (e.g., —OCF3), C1-C6 alkylthio, arylthio, amino, amino(C1-C6)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

Administration and Dosing

Various routes of administration are employed to deliver the compositions disclosed herein, depending on the embodiment. For example, in treatment of certain ocular diseases (e.g., retinal degenerative disorders), injection into a specific region of the eye is used to deliver the compositions disclosed herein. In several embodiments, for example, a direct delivery (e.g., injection) under the macula is used to deliver the compositions to the retina. In several embodiments, delivery is to the vitreous cavity. In several embodiments, delivery to the posterior chamber is performed to deliver the therapeutic compositions to various cell types. In several embodiments, a single injection is sufficient for therapeutic efficacy, while in some embodiments, a plurality of injections is made (e.g., one, or more, injections over a period of time, such as weeks or months). In several embodiments, the duration of efficacy (e.g., the functional lifetime of the compositions) is about 3-4 weeks, about 4-6 weeks, about 6-8 weeks, about 8-12 weeks, about 12-18 weeks, about 18-24 weeks, about 24-48 weeks, about 6 months to about 1 year, and overlapping ranges thereof. In several embodiments, the functional lifetime of the compositions is indefinite, and thus a single administration is used.

In several embodiments, targeting mechanisms, of one kind or another, or combinations, are used to more precisely deliver the compositions disclosed herein. In several embodiments, vesicle transport is used to deliver the compositions. For example, liposomes, exosomes, microvesicles, epididimosomes, argosomes, exosome-like vesicles, microparticles, promininosomes, prostasomes, dexosomes, texosomes, dex, tex, archeosomes and/or oncosomes are used, depending on the embodiment. The vesicles, regardless of their type are, in several embodiments, specifically targeted (or at least preferentially targeted) to a particular cell type. For example, in several embodiments, the retinal ganglion cells are targeted. In some embodiments, other cell types are targeted, in addition to, or in place of retinal ganglion cells, such as, for example, photoreceptors, bipolar cells, amacrine cells, and the like.

Targeting is accomplished, depending on the embodiment, in one or more ways. In several embodiments, markers that are specifically (or at least preferentially) expressed by a target cell can be recognized by antibodies, and such antibodies can be incorporated into a vesicle that carries the photochemical compositions disclosed herein. In several embodiments, unique cell surface markers are employed as targeting agents. In several embodiments, antibodies directed against specific markers are directly coupled to the photochemical compositions. In other embodiments, the antibodies are coupled to a vesicle or other carrier moiety. In some embodiments, markers such as Brn3a, BRN3b, NGF, NSCL2, and/or PKC (as well as, optionally, other markers) are used to target retinal ganglion cells. While multi-chain antibodies are used in some embodiments, in several embodiments, single chain (e.g., camel-type) antibodies are employed.

Peptide targeting is used in several embodiments. For example, in several embodiments, peptides that specifically interact with a desired target cell are identified by library screens. For example, phage libraries are screened, in several embodiments, to identify one or a plurality of peptides that are used to specifically target certain cell types. In several embodiments, yeast two-hybrid screens are used, as well as RNA display, and/or ribosome display, depending on the embodiment. In several embodiments, natural peptides that interact with certain ocular cells are used, while in some embodiments, mutant or synthetic peptides are generated. For example in several embodiments, mutants of natural peptides are generated that reduce and/or eliminate side effects of the natural peptides.

In several embodiments, targeting is accomplished based on the electrical activity of cells. In several embodiments, those that are capable of electrical signaling but show evidence of reduced activity are targeted. In several embodiments, those that are electrically silent, even in the face of normal or hyperstimulation, are targeted. In several embodiments, the compositions disclosed herein can function in a tailored manner to program cells to be responsive to light. In, voltage sensitive cells are targeted (e.g., those that act in response to a change in membrane potential. For example, in several embodiments cells that express voltage gated sodium channels are targeted. In several embodiments, targeting is not only to a specific cell population, but also within a distinct region of the target cell population. For example, certain retinal ganglion cells have a high concentration of voltage gated sodium channels in the axon hillock. Given that the compositions disclosed herein are suitable for electrical manipulation of cells, in several embodiments, specifically targeting such a region of potential high electrical excitability, is particularly advantageous for achieving the desired effect.

Various other types of targeting are used in other embodiments. For example, in several embodiments a magnetic field (produced externally, but focused to an internal target site) can be used to target the compositions disclosed herein. In several embodiments, for example when the compositions are carried by vesicles, the vesicles can be generated to include magnetic particles (for example, superparamagnetic iron oxide). Protein-protein interactions (e.g., a protein coupled to the photovoltaic composition and a protein on a target cell) are used in several embodiments to target the compositions.

In several embodiments, targeting is not performed. However, in some such embodiments, normally functioning cells that take up the composition may adversely react to the function of the composition. For example, in macular degeneration, the centrally located cells are malfunctioning, while peripheral cells function normally. Deployment of the compositions to the normally functioning cells may cause disruption of that normal function. Thus, if specific targeting is not performed, in some embodiments, there is a selective destruction (or disruption) of the functioning of the composition in cells that are normally functioning. Thus, in one embodiment, delivery is non-specific, and then "removal" of the composition from certain cells is specific. In several embodiments, the removal can be performed by exposing the compound to long infrared light (or other light) that is not thermally damaging, but disrupts the structure and/or function of the compound.

In several embodiments, specific targeting is not performed.

Advantageously, the number of molecules delivered to a particular target cell population can be calculated in advance and/or visually confirmed. As such, calculations can be made that allow for the minimal amount of light stimulation to be applied to a subject's eye in order to induce the electrical activity of the cells of the subject's eye (e.g., the retinal ganglion cells). In several embodiments, the ratio of photovoltaic molecule (whether transition metal complex or donor-bridge-acceptor) can be calculated and optimized. In several embodiments, the ratio is about 1 photovoltaic molecule: 1 cell, while in several embodiments, the ratio is about 10:1, about 20:1, about 50:1, about 100:1, about 1000:1 about 10,000:1, about 100,000:1 and overlapping ranges thereof. Greater or lesser ratios may be used, depending on the embodiment.

In several embodiments, the tunability of the lifespan of the activation of the photovoltaic molecule (whether transition metal complex or donor-bridge-acceptor) allows for a tailored activation profile for a particular patient. For example, a donor-bridge-acceptor molecule configured with a longer bridge can increase the lifespan of the activated state of the molecule, such that a greater amount of time elapses from the activation to the deactivation of the molecule (e.g., the "excited state"). In several embodiments, this time is at least about 100 microseconds (sufficient to allow the generation of an action potential). In several embodiments, the excited state lifetime ranges from about 1 to about 200 microseconds. In several embodiments, the lifetime of the dipole generated by the excitation of the molecule (e.g., the charge transfer process) is greater than the excited state lifetime. In several embodiments, the existence of the dipole determines, at least in part, the duration of ion channel opening. Advantageously, the D-B-A molecules generated and used according the disclosure herein, deactivate in a time frame that reduces the risk for ion channel deactivation (e.g., due to being held in an extended open state) and also in a time frame the prevents excessive influx of calcium into the cells, which can be toxic to the cells. Tunability may also be achieved by altering the ligands and the transition metal incorporated into the complexes, thereby altering the emission energy of the complexes.

Tunability of photovoltaic transition metal complexes that are not part of a D-B-A molecule may also be achieved by altering the ligands and the transition metal. For these transition metal complexes, the effects of activation of the molecules can be modulated based on the "dose" administered (e.g., the number of molecules per cell), as discussed above. Moreover, as discussed below, in several embodiments, there are associated devices used in conjunction with these complexes (and the D-B-A) that allow for tailored amplification or retardation of light intensity, thereby imparting another degree of tunability. Dosing regimens are also tailored on a patient by patient basis, in several embodiments, for example based on the severity of disease. For example, in several embodiments, the photovoltaic molecule (whether transition metal complex or donor-bridge-acceptor) is administered at an interval of about 6 weeks to about 2 months, about 2 months to about 4 months, about 4 to about 6 months, about 6 months to about 1 year, or longer. Advantageously, the increased efficacy of the photovoltaic molecules disclosed herein improves patient compliance, as recurrent visits to a medical provider's office are reduced.

Therapeutic Uses

A variety of neurodegenerative diseases may be treated using the compositions and methods disclosed herein. In particular, diseases resulting in, or associated with retinal degeneration, including (but not limited to) artery or vein occlusion, diabetic retinopathy, R.L.F./R.O.P. (retrolental fibroplasia/retinopathy of prematurity), or disease (hereditary in several embodiments), outer retinal degenerative diseases (including, but not limited to) dry AMD, wet AMD, Stargardt's disease, retinitis pigmentosa (RP), and Leber's Congenital Ameurosis. These disease (or corollaries thereof) present, in several embodiments, in different ways such as impaired vision, night blindness, retinal detachment, light sensitivity, tunnel vision, and loss of peripheral vision to total loss of vision. Genetic mutations (either inherited or induced) that affect photoreceptor cells are also treated by the compositions and methods disclosed herein, in several embodiments.

Associated Devices

In some embodiments, the synthetic chemistries disclosed herein are not as biologically efficient as those natural biological pathways that have evolved over millennia. However, the efficacy of the compositions disclosed herein can be augmented by various devices (e.g., prosthetic devices) that are configured to supplement or complement the therapeutic effect of the compositions disclosed herein. In several embodiments, however, the chemistries are sufficiently refined so that such supplementing devices are not used.

Figure 9:
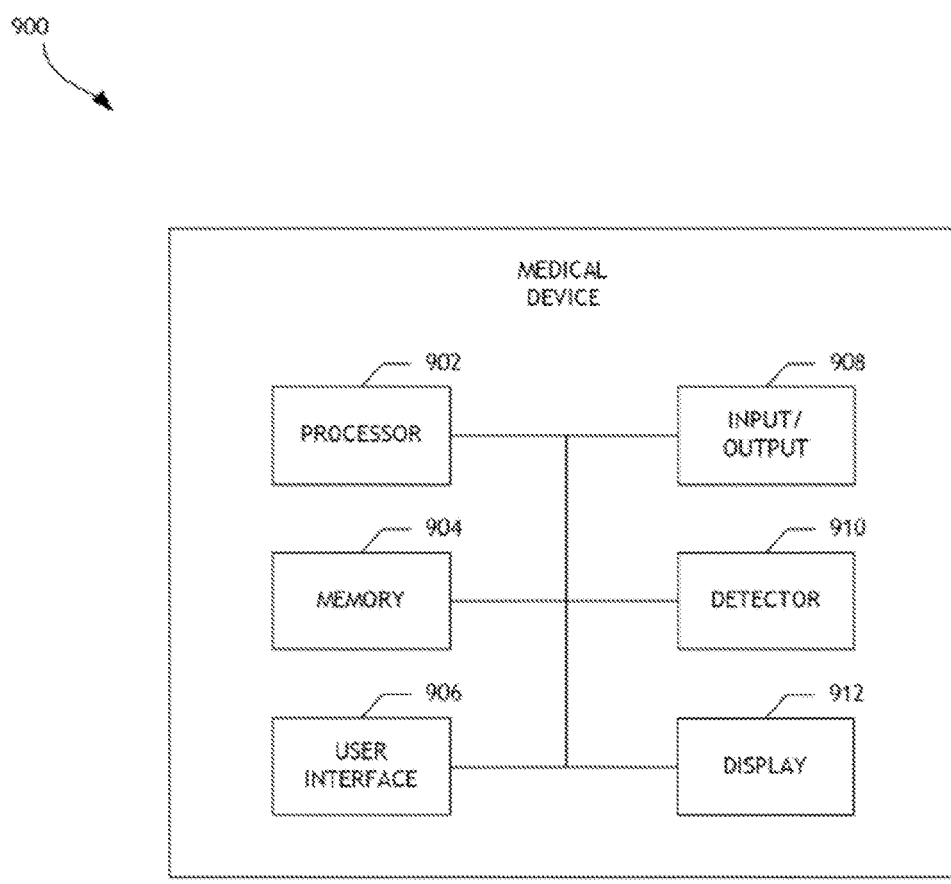
FIG. 9 depicts one schematic of a medical device according to several embodiments disclosed herein.

FIG. 9 illustrates one embodiment of a medical device 900 configured to supplement or complement the therapeutic effect of the compositions disclosed herein. The medical device 900 can perform one or more functions including filtering light, detecting light, processing detected light, and transmitting light. The medical device 900 can, for example, be similar in shape to a hat, mask, glasses, head band, or the like and cover the eyes or face of an individual using the medical device 900. Additionally or alternatively, the medical device 900 can connect to a hat, mask, glasses, or head band worn by an individual. In some embodiments, the medical device 900 detects environmental light proximal to the individual and transmits light indicative of the detected environmental light to the photovoltaic compounds in the eye of the individual, which, as described above, activates the compounds with the end result being the generation of action potentials in the otherwise mis- or non-functional retinal ganglion cells of a subject, thereby allowing the subject to see. For example, in one embodiment, the medical device 900 is a photo-intensifying device employed in order to ensure that there is sufficient light energy entering the eye of the individual to illuminate and activate the various photovoltaic compounds disclosed herein.

In several embodiments, the medical device 900 includes a processor 902, a memory 904, a user interface 906, an input/output 908, a detector 910, and a display 912. Power is provided to the medical device 900 wirelessly, in some embodiments, while in other embodiments, power is provided via a wired connection, such as a disposable or wirelessly rechargeable battery or mains power. In several embodiments, components of the medical device 900 are modular so that the components such as the detector 910 or the display 912 are removable and replaceable with another module, such as another detector or display. In other embodiments, the device is a unitary device. Optionally, such unitary devices have a finite and predictable functional lifespan, and thus, in certain embodiments are disposable. Moreover, in some embodiments, one or more of the components described may optionally be removed without diminishing the functionality of the other components.

In several embodiments, the processor 902 receives signals from and sends signals to one or more other components of the medical device 900 and controls operation of the medical device 900. The processor 902 stores and retrieves data from the memory 904 and communicates and receives information from the user interface 906 and the input/output 908. Further, the processor 902 receives one or more signals from the detector 910 indicative of detected environmental light and/or eye movement of the individual using the medical device 900. The detected environmental light and/or eye movement can be processed and then transmitted to the display 912 for controlling the display and displaying images to the individual using the medical device 900. The processor 902 can include a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof, depending on the embodiment.

In several embodiments, the processor 902 processes one or more signals received from the detector 910 so that the signal provided to the display 912 results in the display 912 transmitting light appropriate for the photovoltaic compounds in the eye of the individual (e.g., in terms of the intensity, frequency, or other characteristic of the light). The processor 902, depending on the embodiment, analyzes detected light and filters, changes wavelengths, shifts frequencies, compresses spectrums, increases or decreases intensities of wavelengths, or adjusts to environments and ambient levels/colors around the medical device 900. The processor 902, in some embodiments, accounts for loss of signal transmission efficiency resulting from the synthetic nature of the photovoltaic compounds (e.g., the inefficient transmission as compared to native biological signaling pathways) and accordingly increases the intensity, frequency, or other characteristic of light displayed by the display 912. In some embodiments, the processor 902 further modifies the detected light based on eye movements, specific needs, or physical limitations of the individual using the medical device 900. In other words, the device, in several embodiments, is configured specifically to the needs of an individual patient.

In several embodiments, the devices operate in conjunction with the photovoltaic compounds to focus (e.g., target) the light from the exterior of the eye (e.g., the image) to a specific layer of the retina. The mammalian retina is made of multiple layers comprising different cell types which enable the retina to break down images into their component elements (e.g., dark object on light background, light object on dark background, edge detection, details, etc.) to perform the overall retinal functions (e.g., functions including motion detection, directional selectivity, local edge detection, looming detection, object motion and saccadic suppression). The various cells of the retinal layers (some of which inhibit neighboring cells, others which excite neighboring cells depending on the cell type activated and the stimulus, e.g., rod or cone stimulus) act in concert to spatially encode the various sub-parts of images entering the eye so that the subparts images can be distilled and the related information sent to the visual cortex via the optic nerve. Because of the stacked nature of the various cell types that make up the retina, the visual world is processed as a series of dynamic neural images. Three of the main cell types of the retina are the photoreceptors, the bipolar cells and ganglion cells. These layers are arranged in a "nested" format, in that multiple photoreceptors feed information to á bipolar cell, and multiple bipolar cells then feed information to a ganglion cell. These cells function, in some cases with other cell types as a sort of functional module that is repeats across the surface of each of the various layers of the retina. Individual differences in the characteristics of each cell class lead to the unique processing characteristics of each neural image throughout the stack.

In several embodiments, the devices function to perform at least a portion of the image processing that the retina (e.g., a healthy retina) would perform on its own, as the photovoltaic compositions and devices are providing input at a point that is later in the overall visual pathway. For example, in several embodiments, some of the edge enhancement that a normal retina would perform will be performed by the device. In several embodiments, the output of the device is a processed image (e.g., processed to perform one or more retinal functions, including but not limited to, motion detection, directional selectivity, local edge detection, looming detection, object motion, and/or saccadic suppression) that is tuned to be input to a particular layer of the retina (e.g., such that the receiving cells of that layer will "understand" the input signal). Thus, the devices are configured to tune their output to particular layers or regions of the retina. Thus, in several embodiments, the devices that amplify (or otherwise process) an incoming signal (e.g., an image) target a processed output version of that signal to a specific portion (e.g., depth) of the retina. In such embodiments, the device facilitates retinal functionality and, in conjunction with the photovoltaic compositions disclosed herein, enables light signals to be processed and translated into nerve stimulation, and eventually sight. In some embodiments, however, the output of the device is provided to the retina, at least in part, in a partially processed form. In other words, in addition to modulating frequency, intensity, wavelength or other light characteristic, and providing a composite image, the device "pre-processes" certain aspects of the incoming image, and provides that processed image data to a specific receiving portion of the retina. So rather than a patient "seeing" an image like a normal healthy eye, the devices, in conjunction with the photovoltaic compositions, insert a processed image (e.g., a checkerboard and/or grayscale image) to a later portion of the visual pathway, thereby bypassing the defective units of the visual pathway. In several embodiments, this allows the patient to have some visual function, whereas in the absence of the methods and/or devices, vision would be non-existent.

In several embodiments, the memory 904 is configured to store data, programs, and settings of the medical device 900. The processor 902, for example, accesses the memory 904 to determine the characteristics of the photovoltaic compounds in the eye of the individual using the medical device 900 to select appropriate intensity levels for light displayed on the display 912. In some implementations, the processor 902 stores images detected by the detector 910 for later viewing, such as for use in troubleshooting. The memory 904 can include Random Access Memory (RAM), flash memory, Read Only Memory (ROM), Electrically Programmable ROM (EPROM), Electrically Erasable Programmable ROM (EEPROM), registers, hard disk, a removable disk, or any combination thereof, and the like.

In several embodiments, the medical device is programmable. In such embodiments, the user interface 906 (at least in part) manages the settings of the medical device 900. The user interface 906 is used to select configurations, as well as manage aspects of operation and performance of the medical device 900. The user interface 906 includes one or more of light-emitting diodes (LEDs), buttons, keys, switches, a joystick, a touchscreen graphical user interface, and the like to enable user input. In some embodiments, the user interface 906 secures the medical device 900 with a passcode to prevent unauthorized access or use of the medical device 900.

In several embodiments, the input/output 908 enables the medical device 900 to communicate with other devices and/or a computer network. The medical device 900 can be programmed after manufacture through the input/output 908, and patient data and settings can be output via the input/output 908, for instance. The input/output 908 can include wireless connections (such as infrared, radio, and microwave receivers or transmitters, and the like), wired connections (such as coaxial cable, fiber optic cable, twisted pair, or USB 2.0 cable, and the like), or connection ports for wired connections.

Figure 10:
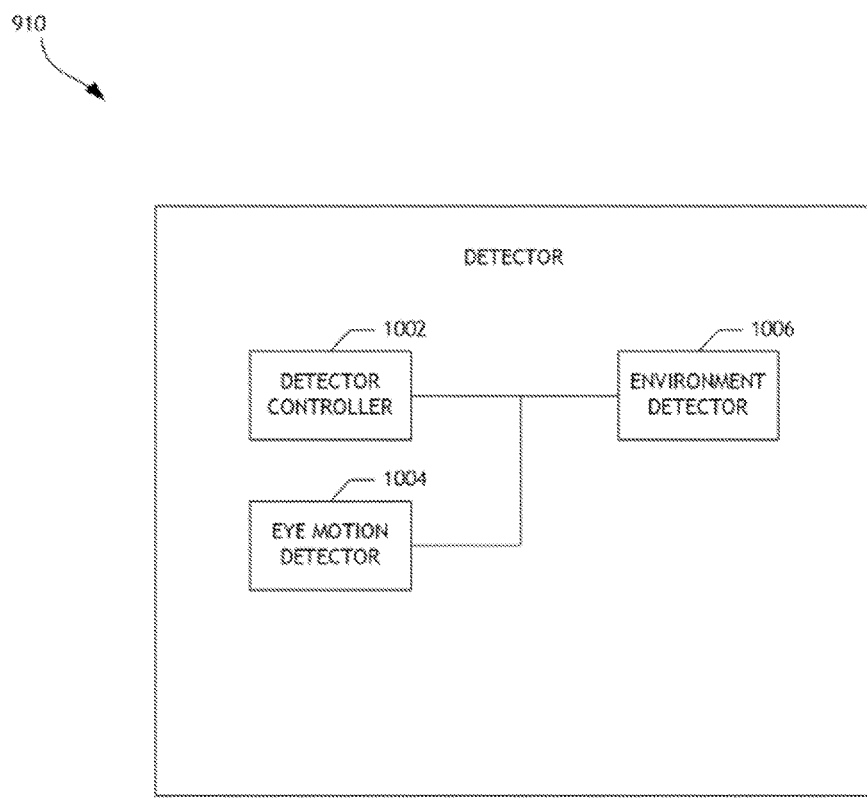
FIG. 10 depicts one schematic of a dectector according to several embodiments disclosed herein.

FIG. 10 illustrates one embodiment of the detector 910 of the medical device 900. In such embodiments, the detector 910 detects both light proximal to the individual and/or eye motion of the individual and generates one or more signals indicative of the detected light and/or eye motion. The processor 902 of the medical device 900 can be the same as or separate from the detector controller 1002. In several embodiments, the detector 910 includes a detector controller 1002, an eye motion detector 1004, and an environment detector 1006.

The detector controller 1002 controls operation of the detector 910, including operation of the eye motion detector 1004 and the environment detector 1006. The detector controller 1002, for example, manages the settings of the detector 910, such as patient or situation specific settings, and sets the focus for the eye motion detector 1004 and the environment detector 1006. In some embodiments, the detector controller 1002 operates one or more positioning components connected to the eye motion detector 1004 and the environment detector 1006 and thereby changes the position or angle of detected light. Further, the detector controller 1002 can encode detected signals before transmitting the signals for processing by the processor 902.

The eye motion detector 1004 detects the position or motion of one or both eyes of the individual using the medical device 900. The eye motion detector 1004, for instance, generates one or more coordinates indicative of the location of each pupil of each eye of the individual. Using the coordinates, the detector controller 1002 can track motion of the individual's eyes and determine which direction the individual is looking. The eye motion detector 1004 can include one or more light detectors such as photodetectors, digital charge-coupled devices (CCDs), or complementary metal-oxide-semiconductors (CMOSs), and the like. Color detection may also be performed using one or more of a Bayer sensor, Foveon X3 sensor, or 3CCD, for instance. The eye motion detector 1004 may detect light in a narrow or wide range of wavelengths of light, including but not limited to infrared, visible, or ultraviolet light.

The environment detector 1006, in several embodiments, detects light proximal to the medical device 900 using one or more detectors. In some embodiments, the environment detector 1006 detects light with two detectors positioned a distance apart approximating the distance between an average adult human's eyes or the eyes of the individual using the medical device 900. Using the two detectors, the environment detector 1006 generates one or more signals indicative of the detected environmental light around the individual. The detector controller 1002, in turn, can control the position, angle, and focus of the detectors of the environment detector 1006 based on the detected eye motion by the eye motion detector 1004. The environment detector 1006 can include one or more light detectors such as photodetectors, digital charge-coupled devices (CCDs), or complementary metal-oxide-semiconductors (CMOSs), and the like. Color detection may also be performed using one or more of a Bayer sensor, Foveon X3 sensor, or 3CCD, for instance. The environment detector 1006 can detect light in a narrow wide range of wavelengths of light, including but not limited to infrared, visible, or ultraviolet light. In several embodiments, the environment detector 1006 is configured to specifically detect and transmit to the user of the device 900 infrared light. In such embodiments, vision at night or in low light (or other conditions that obscure normal vision) is possible based on the infrared spectrum. While in some embodiments, such a configuration is used to supplement the vision of a subject with defective vision, in several embodiments, such a configuration is used in a normal individual (e.g., rescue, medic, and/or military applications).

Figure 11:
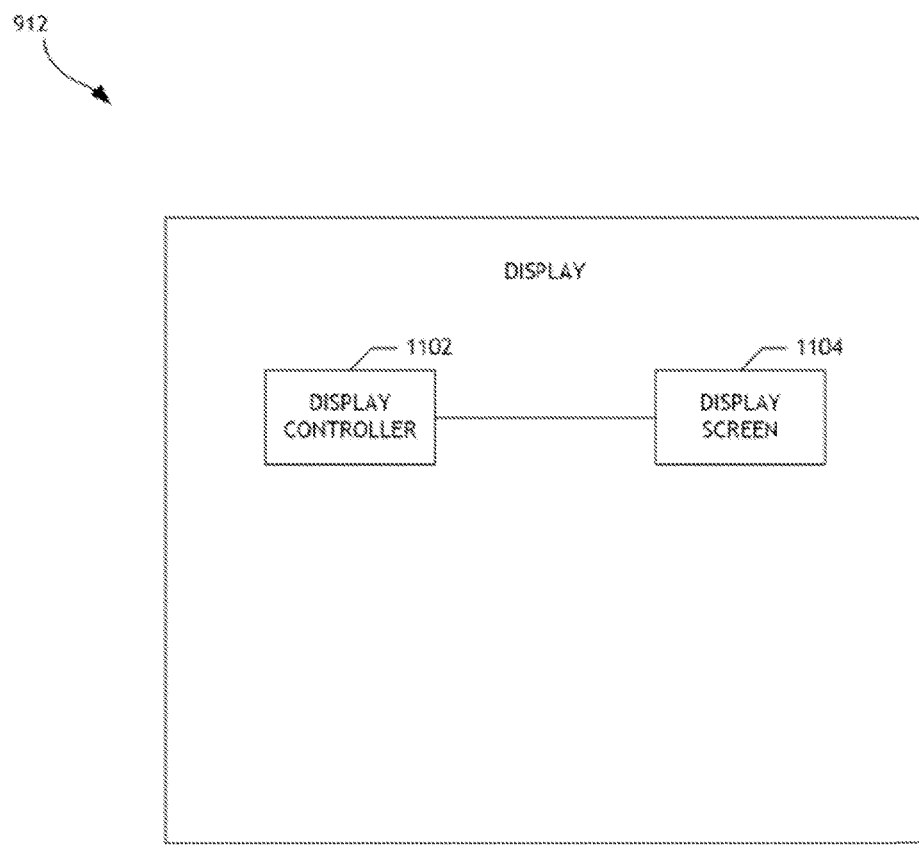
FIG. 11 depicts one schematic of a display according to several embodiments disclosed herein.

FIG. 11 illustrates one embodiment of the display 912 of the medical device 900. The display 912 transmits light to one or both eyes of the individual to illuminate the photovoltaic compounds in one or both eyes, enabling the individual to see. The processor 902 of the medical device 900 can be the same as or separate from the display controller 1102. The display 912 includes a display controller 1102 and a display screen 1104.

The display controller 1102 controls the display of images on the display screen 1104 by controlling the wavelength and intensity of light transmitted by the display screen 1104. The display controller 1102 transmits one or more signals, which include display data and/or control data, to the display screen 1104 causing the display screen 1104 to display images. In several embodiments, the display controller 1102 transmits signals so that the display screen 1104 displays images based on the light detected by the environment detector 1006 after any processing by the processor 902. The display controller 1102 further uses one or more positioning mechanisms, in some implementations, to control the position or angle of the display screen 1104 based on the detected eye movement by the eye motion detector 1004.

The display screen 1104 transmits light to one or both eyes of the individual. The display screen 1104 can include one or more light-emitting diode displays (LEDs), electronic paper (E-Ink), and liquid crystal displays (LCDs), for example. The display screen 1104 can be flexible screen, which wraps around or covers the eyes of the individual using the medical device 900. Such construction, in some embodiments, enables the display screen 11042 to precisely control light transmitted to the individual's eyes. Further, in some embodiments, the display screen 1104 includes a pulse generator, which is tunable, in order to allow fine-scale modulation of electrical activity of targeted cells.

Figure 12:
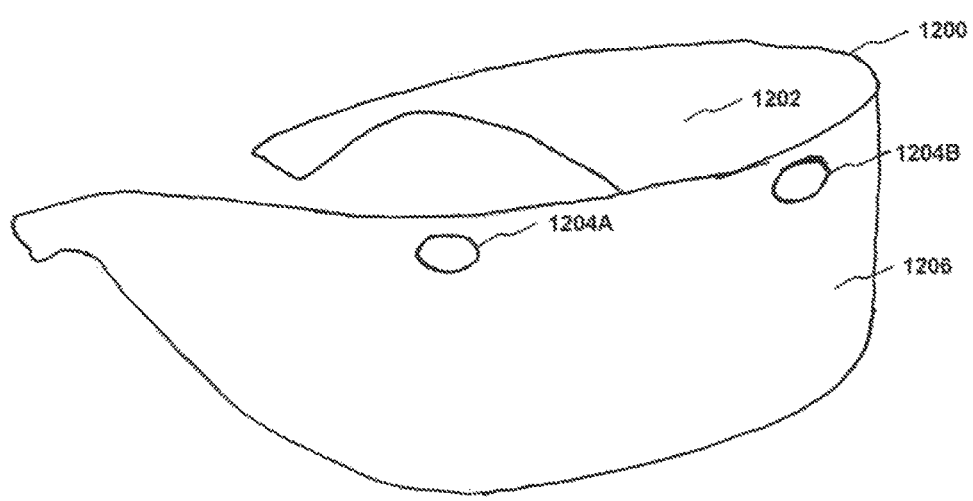
FIG. 12 depicts a schematic of one embodiment of a medical device used for use in conjunction with the compositions disclosed herein.

One example implementation of the medical device 900 are photo-intensifying devices used to ensure that sufficient light energy enters the eye of a subject to illuminate (and thus activate) the various photovoltaic compounds disclosed herein. In several embodiments, these devices are externally positioned (e.g., akin to eyeglasses, 1200, as illustrated in FIG. 12). Alternatively, in some embodiments, the devices are internally positioned (e.g., contact lenses). In several embodiments, the devices are powered by battery power established in the art, solar power, kinetic power, or the like.

However, regardless of the positioning, in several embodiments, photo-intensifying devices comprise a camera module to detect (or otherwise receive) information regarding the environment proximal to the device. In several embodiments, one or more cameras 1204A, 1204B are used to detect the surroundings. In one embodiment, the glasses may have an opaque exterior portion 1206 to block wavelengths of light that may interfere with functioning or responsiveness of the photovoltaic compounds in the eye of the subject. In some embodiments, the exterior portion is substantially opaque. In several embodiments, the photointensifying devices comprise one or more liquid crystal (LCD) displays that displays the images detected from the camera module to the visual pathway of a subject. In several embodiments, the LCD display can be a flexible LCD 1202 that, in certain embodiments, can be wrapped around the interior portion of the glasses, wrap-around LCD display. In other embodiments, other types of LCDs can be used.

In several embodiments, the photo-intensifying devices are configured to account for the loss of signal intensity that may occur in some embodiments in which synthetic compounds are "inefficient" as compared to native biological signaling pathways.

In several embodiments, the photo-intensifying devices comprise a pulse generator, which is tunable, in order to allow fine-scale modulation of electrical activity of targeted cells.

In several embodiments, the photo-intensifying devices comprise at least one sensor unit to detect and adjust output based on ambient light conditions.

In several embodiments, the photo-intensifying devices comprise an element that functions as a pupil tracker. For example, in several embodiments, the photo-intensifying devices function to evaluate (on an ongoing basis) the position of the pupils of a subject, and adjust the display accordingly (e.g., accounting for movement of the subject's eyes over time).

Examples provided below are intended to be non-limiting embodiments of the invention.

Example 1

As discussed above, photovoltaic compositions are used, in several embodiments, to modulate the signaling activity of certain electrically excitable cells in order to synthetically enable the compositions to substitute for functional neuronal tissue. Additional experiments corroborating the above-referenced concepts are provided below.

Methods

Synthesis of [Ru(bpy)$_2$(bpy-C17)](PF6)2

RubpyC17 refers to the compound [Ru(bpy)$_2$(bpy-C17)] (PF$_6$)$_2$. In several embodiments, a 17-carbon tail has been conjugated to one of the three bipyridines to allow for stable insertion into the plasma membrane (FIG. 1A). The bpy-C17 ligand was synthesized following established protocols. Briefly, 0.7 mL lithium diisopropylamide (LDA) (2 M) was added dropwise to a cold tetrahydrofuran (THF) solution of 4,4'-dimethyl-2,2.-bipyridine (0.25 g, 1.3 mmol) under an argon atmosphere. After 30 min, into this brown solution was cannulated a solution of dry THF containing 1-bromo-hexadecane (0.46 g, 1.5 mmol). After the reaction mixture had been stirred for several hours at room temperature, the solvent was removed under vacuum. The residue was then dissolved in CH$_2$Cl$_2$ and washed with 150 mL brine. The product was isolated as an off-white powder. Yield: 345 mg, 65%. The desired metal complex was prepared by refluxing for 3 h a methanol solution containing bpy-C17 ligand (0.10 g, 0.25 mmol) and Ru(bpy)$_2$Cl$_2$ (0.09 g, 0.21 mmol) and was isolated as the PF$_6$ salt. The experimentally determined mass for the product is m/z=411.195 [M$^{2+}$] (calculated: 411.196). $^1$H NMR (DMSO-d$_6$, 400 MHz) 8.82 (4H, d) 8.76 (1H, d) 8.70 (1H, d) 8.15 (4H, t) 7.72 (4H, q) 7.53 (6H, m), 7.37 (2H, t) 2.07 (5H, s) 1.25 (30H, m) 0.84 (3H, t).

Culture of HEK and INS cells

HEK-293T cells were cultured on glass-bottomed culture dishes in the DMEM medium supplemented with 10% fetal bovine serum, 1% penicillin/streptomycin and kept in a humid incubator at 5% CO$_2$. The INS-1 823/13 cells (pancreatic insulin-producing cells, a gift from Chris Newgard) were cultured on glass-bottomed culture dishes in RPMI-1640 medium supplemented with 10% fetal calf serum, 10 mM HEPES, 2 mM L-glutamine, 1 mM sodium-pyruvate, and 0.05 mM 2-mercaptoethanol and kept in a humid incubator at 5% CO$_2$. Fetal bovine serum, fetal calf serum, penicillin/streptomycin, DMEM and RPMI-1640 were purchased from Invitrogen. Other chemicals were purchased from Sigma.

Preparation of Mouse Chromaffin Cells

Mouse adrenal chromaffin cells were dissected from 1-3 month old C57BL/6J mice and were prepared as follows: (1) adrenal glands were removed and placed in cold mouse buffer on ice, (2) fat layers and cortex were removed, (3) medullae were digested by papain followed by collagenase, at 37° C. (though other enzymes may readily be used in other embodiments). Chromaffin cells were plated on matrigel-coated cover slips and placed in a humid incubator, with 5% CO$_2$. Chromaffin cells were patch clamped the next two days following dissection. Mouse buffer consisted of: Locke's solution (154 mM NaCl, 2.6 mM KCl, 2.2 mM K$_2$HPO$_4$.3H$_2$O, 0.85 mM KH$_2$PO$_4$) supplemented with 10 mM dextrose, 5 mM HEPES free acid, 3.7 mM mannitol, and 0.1% phenol red, bubble with 95/5% O2/CO2 for 10 mM, pH was adjusted to 7.2, osmolarity was adjusted (with mannitol) to 320 mOsm, then, in a sterile hood, 0.4% gentamycin and 0.4% pen/strep antibiotics were added. Papain was dissolved in mouse buffer at 25-30 U/ml. Collagenase solution consisted of: 3 mg/ml collagenase (Worthington) in mouse buffer supplemented with 100 µM CaCl$_2$ in mouse buffer. Complete medium consisted of: DMEM supplemented with 10% ITS-X (Invitrogen), 10% AraC, 1% gentamycin, 1% pen/strep, 1% FdU, 10% L-glutamine. Matrigel (BD Biosciences) was diluted 1:8 in DMEM and applied to cover slips for ~1 hr then washed 3× with DMEM.

Imaging RubpvC17 in Live Cells

Cells were imaged at 1-3 days after plating. The glass-bottomed chambers with adherent cells were washed twice with PBS and then filled with standard extracellular solution consisting of 140 mM NaCl, 2.8 mM KCl, 10 mM HEPES, 1 mM MgCl$_2$, 2 mM CaCl$_2$, and 10 mM glucose, pH adjusted to 7.2-7.4 and osmolarity adjusted to 290-310 mOsm. The chamber was then mounted on an Olympus IX70 inverted microscope stage for imaging, using a Cascade 512B EMCCD camera, operated by Metamorph software. Initial imaging was done with cells in extracellular solution without RubpyC17, first under brightfield to evaluate cell health and morphology, then under widefield argon ion laser illumination at 488 nm (Coherent, Innova 90-5, Santa Clara, Calif.), to evaluate autofluorescence. Next, the extracellular solution was removed and replaced with extracellular solution containing the RubpyC17 compound (10 µM in ≤0.01% DMSO, final concentrations). Cell images were then acquired with illumination at 488 nm (collected with a long-pass red emission filter). For electrophysiological experiments, RubpyC17 compound was added to the extracellular solution (2-10 µM in ≤0.01% DMSO, final concentrations as indicated) and cells were incubated for 1.5-45 min, as indicated, then washed with extracellular solution without RubpyC17. Some chromaffin cells were also exposed continuously to 490-900 nM RubpyC17-containing extracellular solution.

Whole Cell Patch Clamp Electrophysiology

Membrane potential was monitored using whole cell patch clamp in current-clamp mode. Cultured cells (INS and HEK293) were plated on a glass-bottomed culture dishes 1-3 days prior to recording. Cells were incubated in standard extracellular solution with or without 10 µM RubpyC17 compound for approximately 1.5-2 minutes, then washed and incubated with standard extracellular solution without additional supplementation, or with 2-5 mM ascorbate, 100 µM sodium ferrocyanide, or 100-200 µM potassium ferricyanide, as indicated. The chamber was transferred to the microscope stage. Extracellular solution consisted of 140 mM NaCl, 2.8 mM KCl, 10 mM HEPES, 1 mM $MgCl_2$, 2 mM $CaCl_2$, 10 mM glucose, pH adjusted to 7.3, and osmolarity adjusted to 300-310. Conventional whole-cell patch clamp recordings were performed with an EPC-9 amplifier and Pulse software (HEKA Electronics). Pipette electrodes of 1.8-3.5 Mohm were fire polished before use. Intracellular solution consisted of: 145 mM KCl, 10 mM NaCl, 1 mM $MgCl_2$, 1 mM EGTA, 2 mM ATP, 0.3 mM GTP and 10 mM HEPES, pH adjusted to 7.3 and osmolarity adjusted to 290-300 mOsm. To monitor changes in membrane voltage/potential, cells were patch clamped in current-clamp mode. Access resistances were in the range of 3-8 Mohm. Using Pulse, membrane potentials were recorded before, during and after illumination by the argon ion laser at 488 nm with an irradiance value of 0.458 $mE\ s^{-1}\ m^{-2}$ or by a xenon lamp source through a 470/40 nm bandpass excitation filter with an irradiance value of 0.480 $mE\ s^{-1}\ m^{-2}$. The duration of illumination varied and the timing is indicated by bars on the figures.

Perforated Patch Clamp Electrophysiology

Action potentials in chromaffin cells were monitored using perforated patch clamp electrophysiology in current-clamp mode, using an EPC10 amplifier and Pulsemaster data acquisition software (HEKA electronics). A coverslip containing mouse chromaffin cells was transferred to a recording chamber and perfused with extracellular solution. Extracellular solution consists of 140 mM NaCl, 2.8 mM KCl, 10 mM HEPES, 1 mM $MgCl_2$, 2 mM $CaCl_2$, 10 mM glucose, pH adjusted to 7.3, and osmolarity adjusted to 290-300 mOsm. Intracellular solution consisted of 145 mM KCl, 10 mM NaCl, 1 mM $MgCl_2$, and 10 mM HEPES, pH adjusted to 7.3 and osmolarity adjusted to 290-300 mOsm. Perforation solution was prepared by adding 4.5 µl of 125 mg/ml stock of amphoterecin B (Sigma) in DMSO to 1.8 mls of intracellular solution, and homogenizing for 5-10 s. Perforation was achieved within 3-10 min following gigaseal formation. Series resistances were in the range of 8-22 Mohm. Light stimulation in the blue spectrum originated from a xenon lamp source with an irradiance value of 0.480 $mE\ s^{-1}\ m^{-2}$ through a 470/40 nm bandpass excitation filter. The duration of illumination varied and is indicated by bars on figures.

Amperometry

Carbon fiber electrodes were prepared using established methodology and coupled to an EPC10 amplifier. A+800 mV constant voltage was applied to the electrode relative to the Ag/AgCl bath electrode. The amperometry recordings were sampled at 4 kHz using Pulsemaster (HEKA). Extracellular composition consisted of 120 mM NaCl, 20 mM KCl, 10 mM HEPES, 1 mM $MgCl_2$, 2 mM $CaCl_2$, 10 mM glucose, pH adjusted to 7.2-7.4, and osmolarity adjusted to 290-300. Light stimulation in the blue spectrum originated from a xenon lamp source through a 470/40 nm bandpass excitation filter. The duration of illumination varied and is indicated by bars on figures.

Data Analysis

Data are represented as means with the standard error of the mean (SEM) and were statistically compared using unpaired, two-tailed Student's t test.

Results and Discussion

Membrane integration of RubpyC17

Figure 1D:
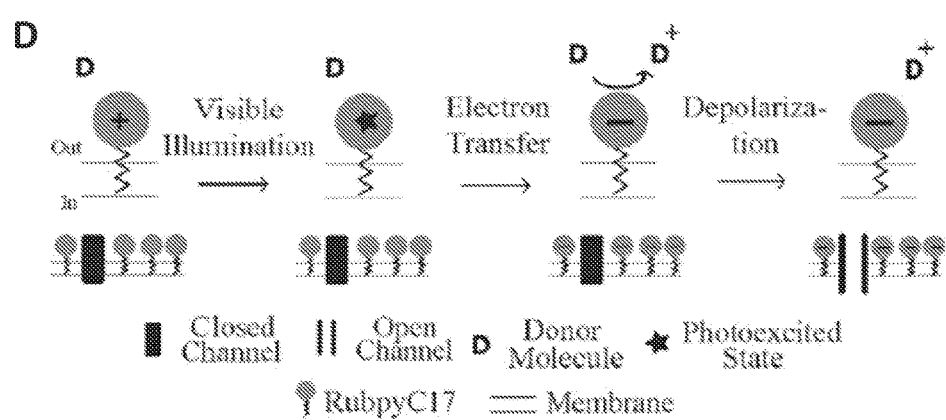

The excitation and emission spectra of RubpyC17 are shown in FIG. 1A. The chemical structure of RubpyC17 is shown in FIG. 1B. RubpyC17 applied to the bath at a final concentration of 10 µM rapidly and stably incorporates into mammalian cell membranes as shown by plasma membrane-localized luminescence (FIG. 1C). Illustrated here are rat insulinoma INS cells (FIG. 1C, top), human embryonic kidney (HEK293T) cells (FIG. 1C, middle), and primary cultured mouse chromaffin cells (FIG. 1C, bottom). None of these cell types exhibited significant auto-fluorescence or auto-luminescence in the red channel, as shown by lack of emission collected from cells not exposed to the RubpyC17 compound. All cell types preserved morphology for at least 10 minutes. Incorporation into the plasma membrane was stable as membrane luminescence was still observed at 10 minutes after RubpyC17 removal from the bath solution. One embodiment of the possible light-induced electron transfer is depicted in FIG. 1D.

Light-Triggered Changes in Membrane Potential

Whether cells treated with RubpyC17 exhibit light-induced membrane potential changes was investigated. Initial attempts were tied to INS and HEK cells, both cells that are not excitable under normal conditions (INS cells were maintained in low glucose <3 mM to prevent action potentials). The cells were incubated in 10 µM of RubpyC17 compound for approximately 2 minutes then washed with standard extracellular solution, supplemented with 2 mM ascorbate. It was hypothesized that when RubpyC17 is incorporated into the cell membrane, illumination would induce accumulation of negative charges at the outer face of the cell membrane, due to transfer of an electron from ascorbate to the photoactivated RubpyC17 resulting in membrane depolarization. To monitor the plasma membrane potential, the cells were patch-clamped in whole-cell configuration in current-clamp mode and membrane voltages were recorded while illuminating the cell at 488 nm (0.46-0.48 $mE\ s^{-1}\ m^{-2}$), though other wavelengths are useful, depending on the embodiment.

Figures 2A, 2B, 2C, 2D:
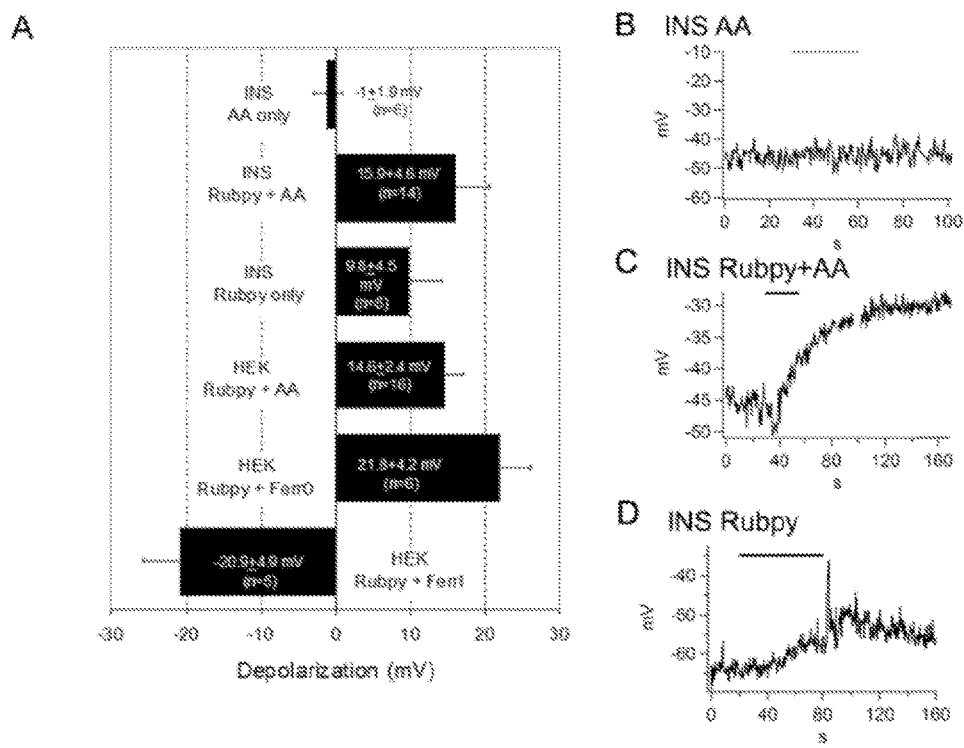
FIGS. 2A-2G depict bi-directional control of membrane voltage by light in cells pre-incubated with RubpyC17.
Figures 2E, 2F, 2G:
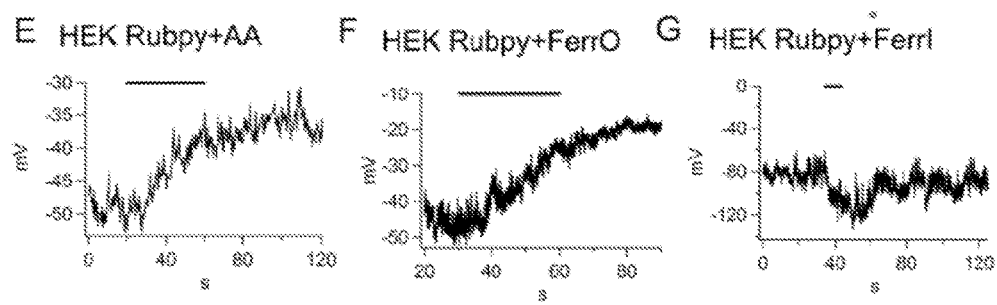

Upon illumination, the membrane potential of INS cells increased by an average of 15.9+4.6 mV in the presence of ascorbate (FIG. 2A,C). In the absence of ascorbate, INS cells incubated with RubpyC17 still showed a modest increase in membrane potential upon illumination (average of 9.8+4.5 mV) (FIG. 2A, D). Similarly, HEK293 cells also showed light-induced depolarization of 14.6+2.4 mV in the presence of ascorbate (FIG. 2A, E). Control INS cells not exposed to the RubpyC17 compound showed no change in membrane potential upon illumination, with or without ascorbate (FIG. 2A, B). The light-induced depolarization was also observed using ferrocyanide as reductant (FIG. 2A, F). These experiments demonstrate, in accordance with several embodiments, the transition metal wire compositions disclosed herein are able to functionally interact with a cell and allow the generation of action potentials in response to illumination.

To further test whether the change in the membrane potential was caused by electron charge transfer between the sacrificial redox molecules and the light-activated RubpyC17 compound, the reductant molecules in the extracellular solution were replaced with oxidant molecules. It was hypothesized that such an alteration would lead to hyperpolarization instead of depolarization upon illumination. Indeed, in the presence of 100 uM ferricyanide in the extracellular solution, illumination of cells pre-treated with RubpyC17 induced a hyperpolarization of 20.9+4.9 mV (FIG. 2A, G).

It was discovered that luminescent cells undergo depolarization when illuminated for 25 seconds or longer when reductants (e.g., ascorbate) are present or for 10 seconds or longer when oxidants (e.g., ferricyanide) are present (FIG. 2A). Other oxidants or reductants are used in several embodiments, such as those that are, normally present (or biologically compatible) in the environment of a certain target tissue. In several embodiments, it is possible that light-induced depolarization or hyperpolarization amplitude or rate is controlled by varying illumination time or intensity. Moreover, the present example demonstrates that RubpyC17 is capable of consistently conferring light-sensitivity to cells that normally do not respond to light, such as, for example, retinal cells that are diseased or damaged.

Light-Triggered Action Potentials

Figures 3A, 3B:
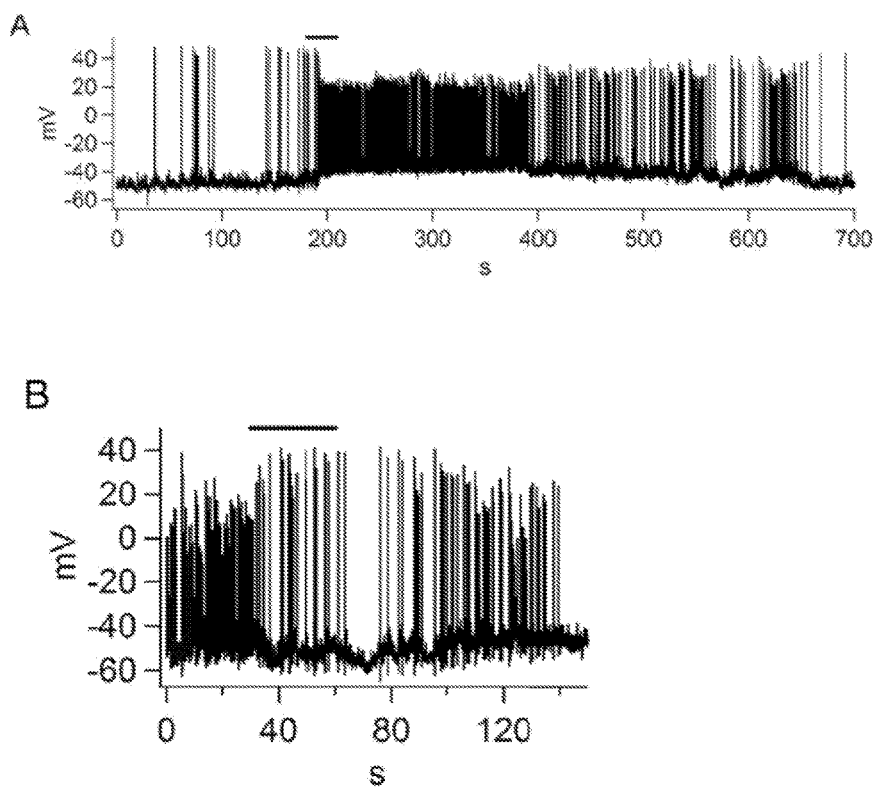
FIGS. 3A-3E depict bi-directional control of action potential firing rate in mouse chromaffin cells pre-incubated with RubpyC17.
Figure 3C:
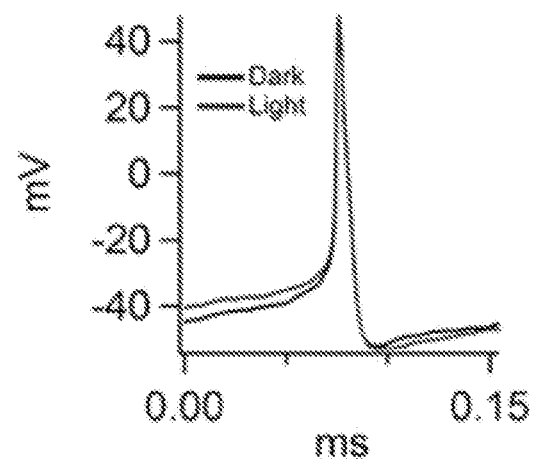
Figure 3D:
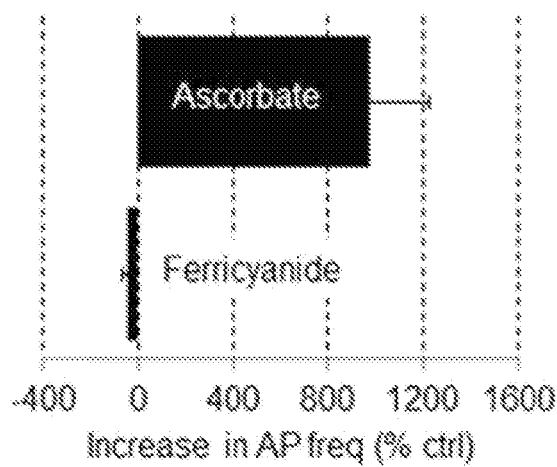

The behavior of excitable cells (cells capable of firing action potentials) treated with RubpyC17 was next investigated. Perforated patch clamp recording was performed on mouse adrenal chromaffin cells pretreated with 450-900 nM RubpyC17 for 15-30 minutes before beginning electrophysiological recordings. In the presence of the reductant ascorbate (5 mM), light illumination triggered action potentials or increased the rate of action potential firing most consistently with cells pretreated with 900 nM RubpyC17 (FIG. 3A,D). A slow, gradual reversal, on the order of seconds after light illumination was terminated (FIG. 3A), was observed. There was no change in the shape of action potential waveforms due to light illumination (FIG. 3C).

In the presence of the oxidant ferricyanide (100 µM), light illumination decreased the rate of action potential firing (FIG. 3B, D) in mouse chromaffin cells. This is consistent with the observation that illumination of RubpyC17-treated INS cells in the presence of ferricyanide resulted in hyperpolarization. The dampening effect on action potential firing in chromaffin cells is slowly reversed upon termination of light illumination (FIG. 3B). Increasing the ferricyanide concentration from 100 to 200 µM further suppressed action potential firing, but also caused adverse effects on cell health such that consistent maintenance of a stable seal in all cells tested (not shown) was not achieved.

Figure 3E:
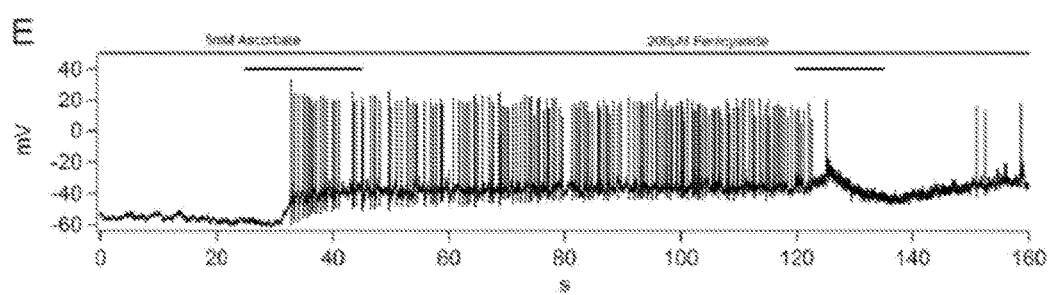

This effect on action potential firing was also observed when the cells were transiently exposed to higher concentration of RubpyC17 (2 µM) for 1.5 min prior to recording (FIG. 3E). Action potential firing rate at a single chromaffin cell that was transiently exposed to 2 µM RubpyC17 undergoes light-induced increase and then light-induced decrease, when the extracellular solution initially containing the reductant ascorbate is changed for one containing the oxidant ferricyanide (FIG. 3E).

Light-Triggered Secretion

Figures 4A, 4B:
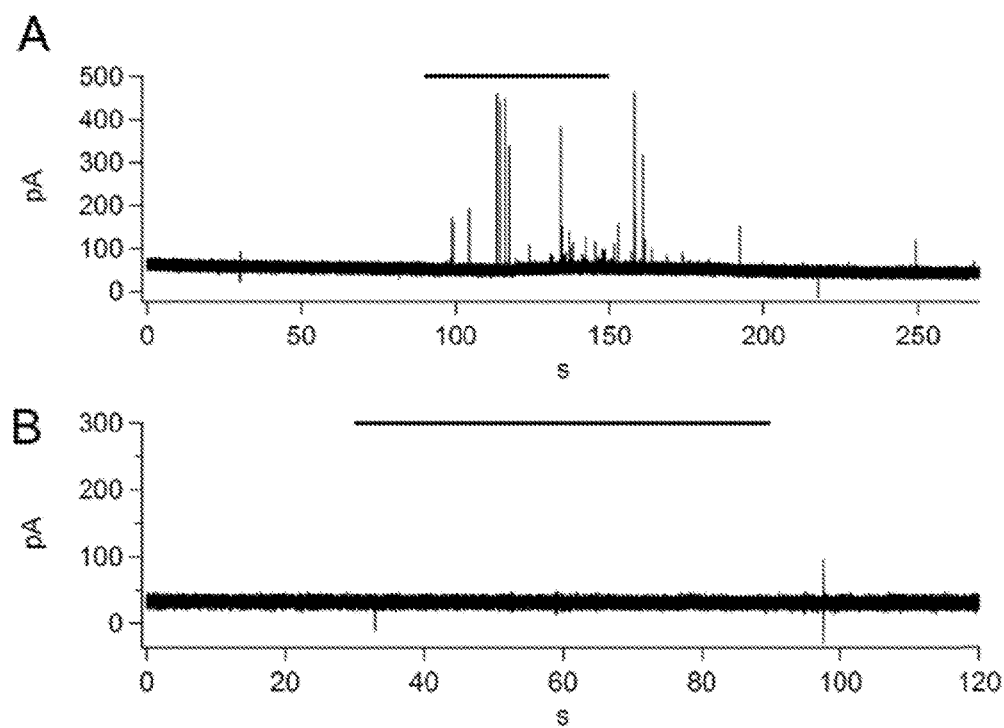
FIGS. 4A-4D depict light-triggered secretion in mouse chromaffin cells pre-incubated with RubpyC17.
Figure 4C:
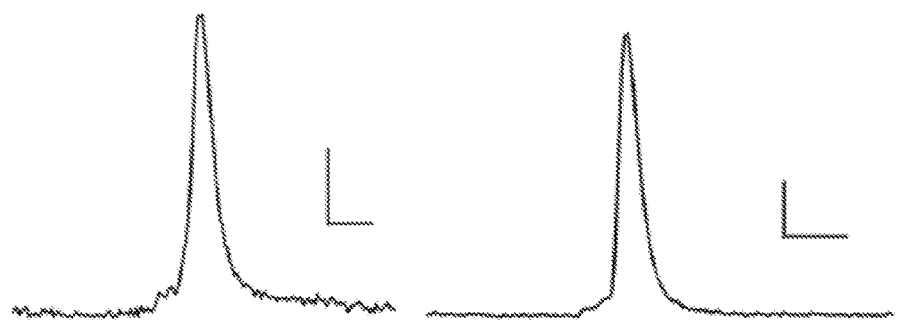
Figure 4D:
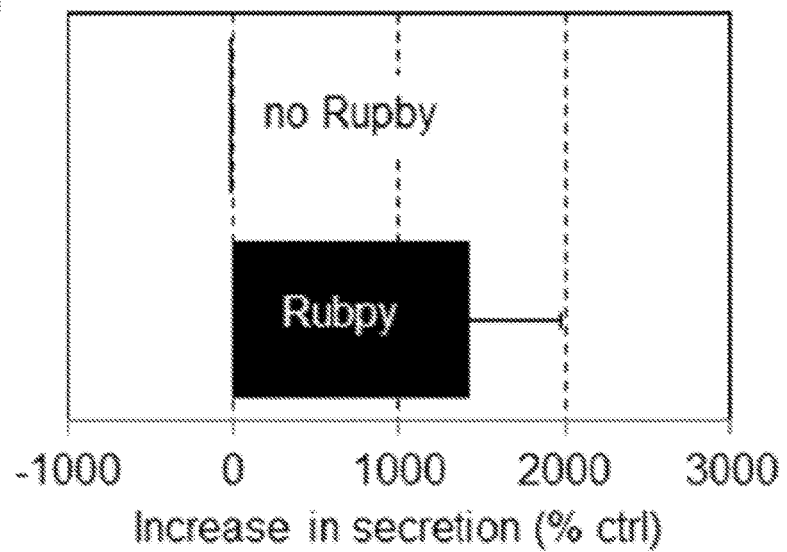

Action potential firing triggers secretion of norepinephrine and epinephrine from adrenal chromaffin cells, which can be readily detected by the technique of carbon-fiber amperometry, thus serving as a surrogate to detect action potential firing. Mouse chromaffin cells pretreated with 2 µM RubpyC17 and illuminated at 488 nm exhibited numerous amperometric current spikes, indicative of vesicular secretion (FIGS. 4A, D). Control chromaffin cells not treated with RubpyC17 did not secrete in response to light (FIGS. 4B, D). Out of 18 RubpyC17-loaded cells tested, 15 cells (83%) experienced increased secretion by at least 100-fold during light illumination. Unlike the changes in light-induced depolarization, light-induced changes in secretion appeared to be more transient. One possible explanation for this is that at any moment in time, there are only a small number of release-competent vesicles—the so-called readily releasable pool of vesicles—and maintained stimulation causes rapid depletion of the readily releasable pool of vesicles in the initial phase of stimulation.

Mechanism of Action

The data presented above demonstrate that the light-induced membrane potential changes are due to intermolecular electron transfer from a sacrificial redox molecule and the membrane-anchored RubpyC17 resulting in a change in the charge capacitatively stored on the cell membrane. The following two potential alternative explanations were then evaluated: (1) light-induced direct interaction between RubpyC17 and ion channels, and (2) light-induced pore formation in the plasma membrane.

Figures 5A, 5B:
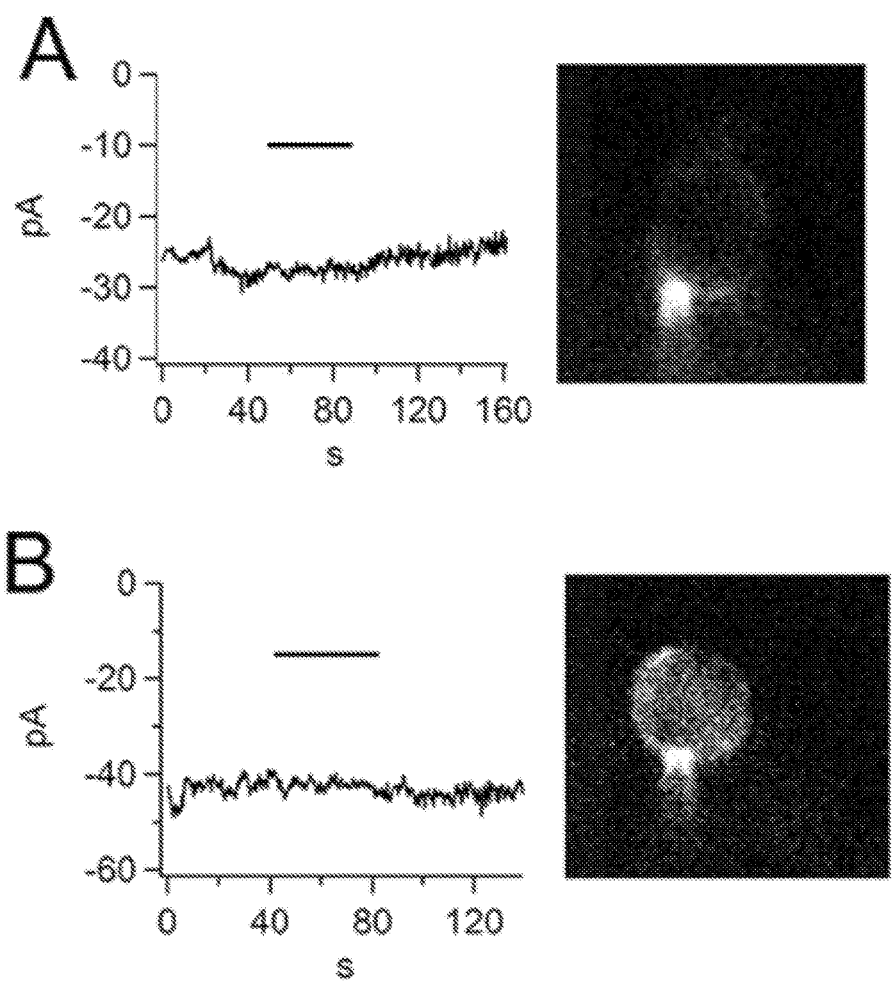
FIGS. 5A-5H depict data from various experiments related to characteristics of RubpyC17-loaded cells.
Figure 5C:
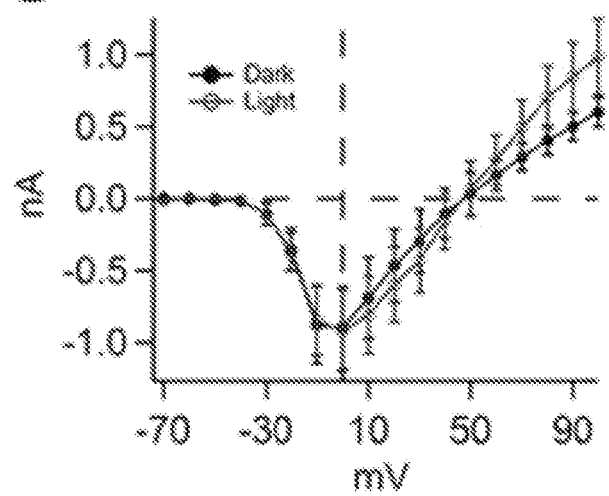
Figure 5D:
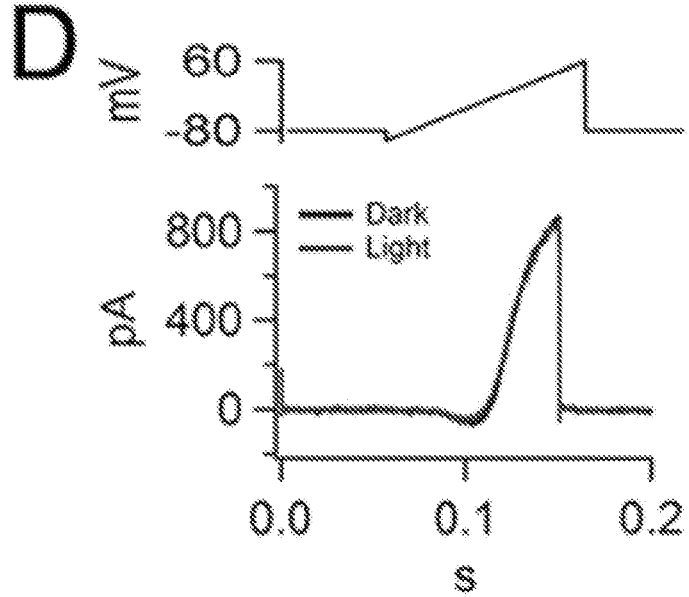
Figure 5E:
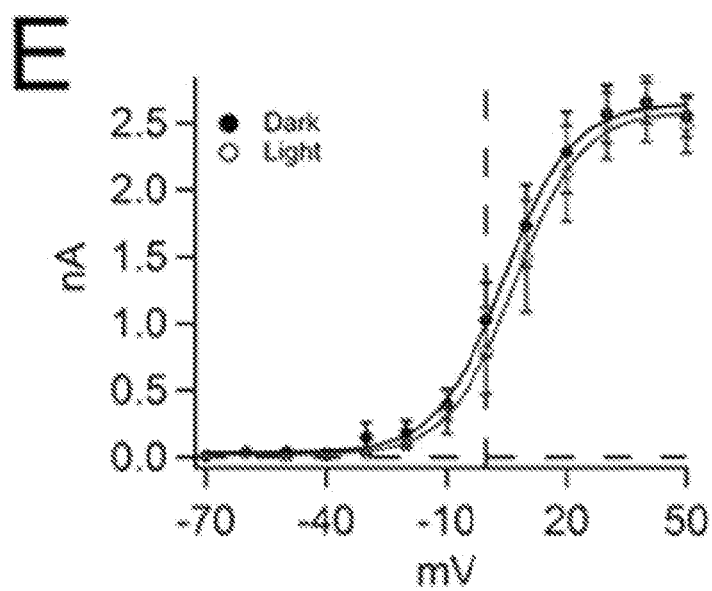

To examine whether light-activated RubpyC17 can directly interact and open or block endogenous ion channels, HEK293T cells were preincubated with RubpyC17, and patch-clamped in a voltage-clamp configuration. Voltage-clamp configuration allowed the cells to be clamped at a potential where most voltage-gated ion channels are closed (approximately −80 mV). Cells treated with RubpyC17 did not exhibit light-induced changes in membrane current (FIGS. 5A, B). The current-voltage relationship (FIGS. 5C, D) as well as the steady-state voltage-dependent activation curves of RubpyC17-treated chromaffin cells in voltage-clamp mode before and during light illumination (FIG. 5E). These data indicate that the integration of RubpyC17 in the plasma membranes does not alter the biophysical properties of endogenous ion channels.

Finally, to test whether illumination of RubpyC17 incorporated in cell membranes causes nonspecific membrane poration or other damage, 18 µM RubpyC17 was loaded inside a patch pipette and attached to a cell (gigaseal formation) in the cell-attached configuration. This is the same configuration used routinely for perforated-patch recording This approach allowed illumination of the cell with blue light and then repeated step hyperpolarization was applied while monitoring the capacitance current transient due to charging the small membrane patch capacitor through the series resistance (mainly the electrode series resistor). If RubpyC17 permeabilizes the membrane of the attached patch, the conductance through the patch should increase, opening a path for current to charge the capacitor of the rest of the whole cell membrane; the capacitive charging transient should grow larger and the time constant of the decay should increase.

Figure 5F:
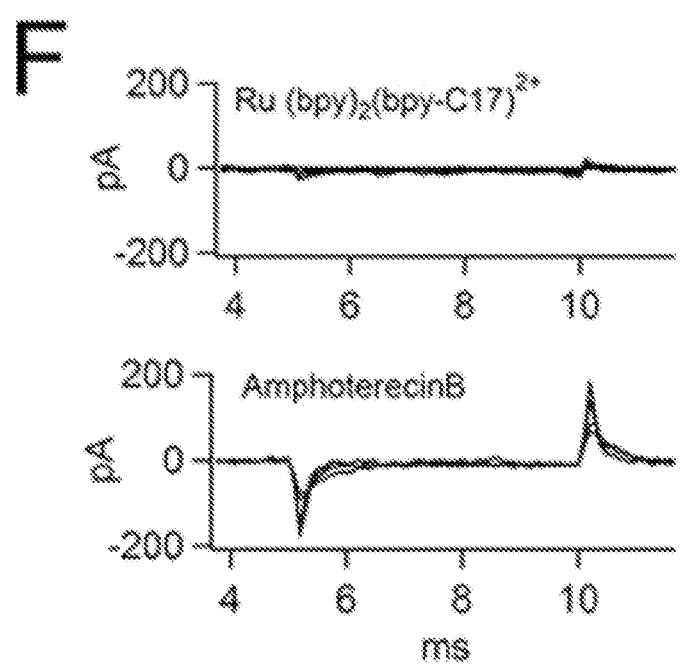

As shown in FIG. 5F (top), an increase in the capacitive charging transient was not detected, which indicates that RubpyC17 does not cause significant membrane damage. As a positive control, the same experiment was performed with amphotericin B, an antifungal antibiotic, which is used to create holes in cell membranes for perforated-patch experiments. Perforated-patch recordings allow current to flow through tiny holes in the membrane patch encircled by the pipette rim at the membrane, but prevent loss of critical cytosolic components (like ATP and proteins) from out of the cell and into the pipette. These recordings were used routinely to make recordings of action potentials. Within 5 minutes of gigaseal formation with amphotericin B in the pipette, a sizable capacitive charging transient (FIG. 5F, bottom) was observed, whereas with RubpyC17, a noticeable change in the capacitance transients even 10 minutes after gigaseal formation was not seen. (FIG. 5F, top).

Figure 5G:
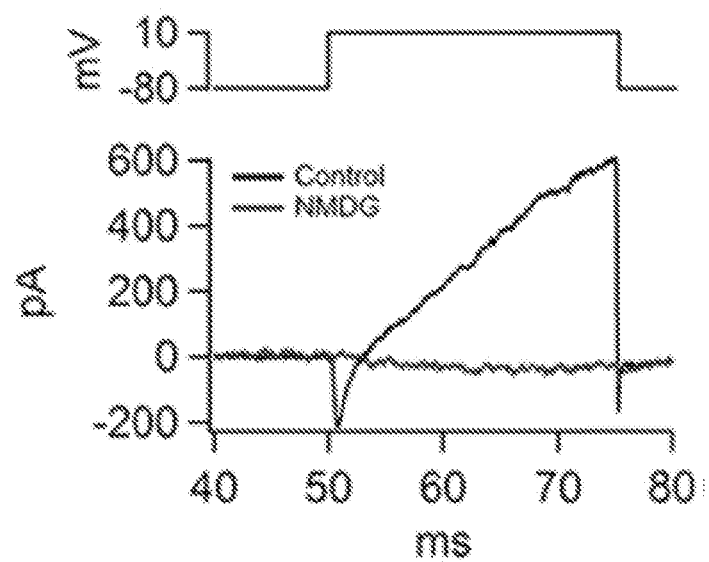
Figure 5H:
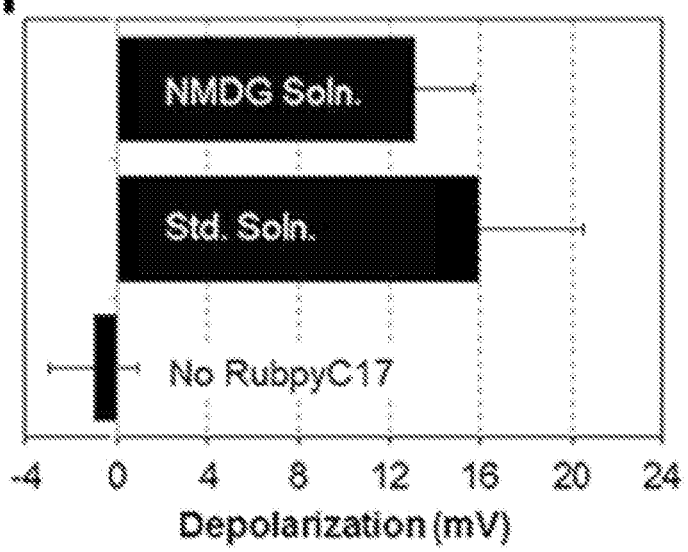

As a final test to rule out the possibility that membrane potential changes were due to pore formation, the permeating ions (potassium and sodium) from the internal and external solutions were replaced with non-permeating ions (cesium and N-methyl-D-glucamine or NMDG). The light-triggered depolarization in RubpyC17-loaded INS cells still persisted when solutions containing non-permeating ions were used (FIGS. 5G, H). This indicates that the membrane depolarization arises independent of transmembrane ion flux.

The present example demonstrates synthesis and characterization of a photovoltaic nanoswitch RubpyC17 and has demonstrated that it (1) integrates rapidly and stably into living cell membranes, (2) enables light-induced membrane potential changes, for which the direction of the change is dependent upon the nature (e.g., reductant versus oxidant) of a soluble redox partner present in solution, (3) facilitates light-induced changes in action potential firing rate in excitable cells, and (4) facilitates light-induced secretion from excitable secretory cells, such as chromaffin cells.

There are several notable differences between RubpyC17 and the other previously characterized small diffusible photoswitch compounds. Each has advantages and disadvantages, which may determine the choice for a particular application. Depending on the embodiments, other ligands bound to transition metals may also be used to accomplish the same (or other) nanoswitches with desirable properties.

RubpyC17 integrates consistently, rapidly and stably in the plasma membrane of a range of mammalian cells, including INS, HEK293, and primary cultured chromaffin cells. Based on its structure, RubpyC17 should be able to integrate into the membrane of most cell types. Screening for integration into cell membranes is rapid, because RubpyC17 luminesces strongly in the red spectrum when illuminated. This is in contrast to azobenzene-based compounds that do not luminesce. Although the ferrocene-porphyrin-C60 luminesces in solution, its luminescence is quenched once delivered to the plasma membrane. Having direct evidence that the complex is in the cell membrane speeds experimental protocols and enables ruling out absence of membrane-associated complex when a cell does not respond to illumination.

The mechanism of action of RubpyC17, unlike the azobenzene photoswitches, does not involve direct blocking or unblocking of specific ion channels. Rather, in several embodiments, the light-induced membrane potential change is the consequence of electron transfer to or from the ruthenium complex at the outer face of the cell membrane, which charges up the membrane capacitor and thereby indirectly activates or inhibits voltage-gated ion channels. This is strongly supported by the observation that light induces depolarization in ruthenium complex-treated cells when ascorbate (reductant) is in the bath (FIGS. 2A, C, and E), whereas light induces hyperpolarization when ferricyanide (oxidant) is in the bath (FIGS. 2A, G). Furthermore, ion channels are not needed for the membrane potential changes (FIGS. 5G, H), and membrane damage is not involved (FIG. 5F). In contrast, the mechanism of action of soluble azobenzene photoswitches containing a quaternary ammonium moiety is the light-induced unblocking and blocking of potassium channels. Similarly, the mechanism of action of ferrocene-porphyrin-C60 is the light-induced inhibition of potassium channels that only provides unidirectional control of membrane potential (light-induced depolarization).

To reach a maximum effect, the light-triggered depolarization in RubpyC17-treated cells requires on the order of 30 seconds of continuous illumination at 0.46-0.48 mE s−1 m2 (FIGS. 2B-F) The time course observed is dependent on several factors, and may be greater or lesser during in vivo applications. One, it is related to the probability of photon absorption per unit time by membrane-associated RubpyC17, which depends on the concentration of RubpyC17, the partitioning into the membrane, and the photon flux. Two, it is related to the diffusional collision between the soluble redox partner and photoactivated RubpyC17 before the complex has undergone another photophysical fate, which depends on the density of RubpyC17 in the cell membrane and its membrane diffusion coefficient. Lastly, the time course is related to the probability of intermolecular electron transfer in the case of a collision, and this also depends on the redox partner (e.g., ascorbate) not participating in competing redox reactions in the membrane or bath solution, which would reduce its effective concentration. Notably, the rate of electron transfer with ascorbate appears slower than with ferricyanide. It is hypothesized that the difference in kinetics is due to the higher efficiency of electron transfer from the photo-activated RubpyC17 to the oxidant ferricyanide ($k_{et}$~$6.5 \times 10^9$ $M^{-1}$ $s^{-1}$ aqueous solution), as compared to the electron transfer from the reductant ascorbate ($k_{et}$~$2 \times 10^7$ $M^{-1}$ $s^{-1}$) to the photo-activated RubpyC17.

The light-induced depolarization of RubpyC17-treated cells in the presence of reductants appears to be irreversible (FIGS. 2B-F) or reverses at a very slow rate (FIGS. 3A-C), as was reported also for ferrocene-porphyrin-C60. This may be due to transfer of the electron from RubpyC17 to an endogenous membrane molecule that maintains the negative charge at the outer face of the cell membrane capacitor. The presence of endogenous membrane components capable of participating in reduction-oxidation activity is likely, since RubpyC17-treated cells without the addition of excess reductant or oxidant still undergo depolarization in response to light (FIGS. 2A, D), though to a smaller extent as compared to in the presence of a soluble redox partner.

Based on the continued viability of chromaffin cells after incubations of ~30 min with RubpyC17, as evidenced by maintained light-induced action potential firing and secretion (FIG. 3), it seems unlikely that RubpyC17 causes major non-specific damage to the cell, thereby suggesting that these compositions are viable for use in vivo, in several embodiments. However, in several embodiments, other organic ligands coupled to other transition metals are also used, with reduced and/or non-existent adverse side effects. The generation of non-specific damage by light-activated RubpyC17 was ruled out by experiments showing that high concentrations of RubpyC17 failed to perforate the cell before or during light illumination, as measured in cell-attached mode (FIG. 5D). Excessive and prolonged whole cell incubation with RubpyC17 (e.g., >10 µM for >5 min) may result in cell toxicity, since a stable gigaseal cannot be stably maintained in those cells. At this time, the mechanism behind the adverse effects on cell health upon RubpyC17 overexposure is not yet fully known. Since perforation was not achieved when a small patch of membrane was exposed to a high dose of RupbyC17, it was hypothesized that when an entire cell is overexposed to RubpyC17, there may be sufficient random interactions between excess RubpyC17 complex and endogenous surface molecules (i.e., proteins, carbohydrates, sugars), triggering signals that lead to cell health deterioration. However, when used in its appropriate dose range (e.g., <about 10 µM for cell lines and <about 2 µM for primary cells, according to one embodiment), RubpyC17 is tolerated by cells and consistently confers light sensitivity.

In summary, metal-diimine complexes function as photovoltaic nanoswitches that serve as a convenient tool for remote optical control of cellular electrical activity. Unlike the prevailing tools for remote optical control, the metal-diimine complexes do not require expression of high levels of a foreign protein or excitation by cytotoxic wavelengths. The potential for analog control by varying light illumination intensity and duration using this complex is worth exploring. Initial data shows that increasing the ferricyanide concentration from 0.1 mM to 0.2 mM further suppressed action potential firing. Many other photovoltaic nanoswitches do not offer rapid on-off switching of cellular electrical activity, unlike the compositions disclosed herein, but compositions, such as those disclosed herein, in which both electron donor and acceptor moieties are joined in a single molecule may address many of the current limitations and are useful in methods of restoring to or generating in, cellular electrical activity.

Example 2

Synthesis of the D-B-A Complex

Figure 8:
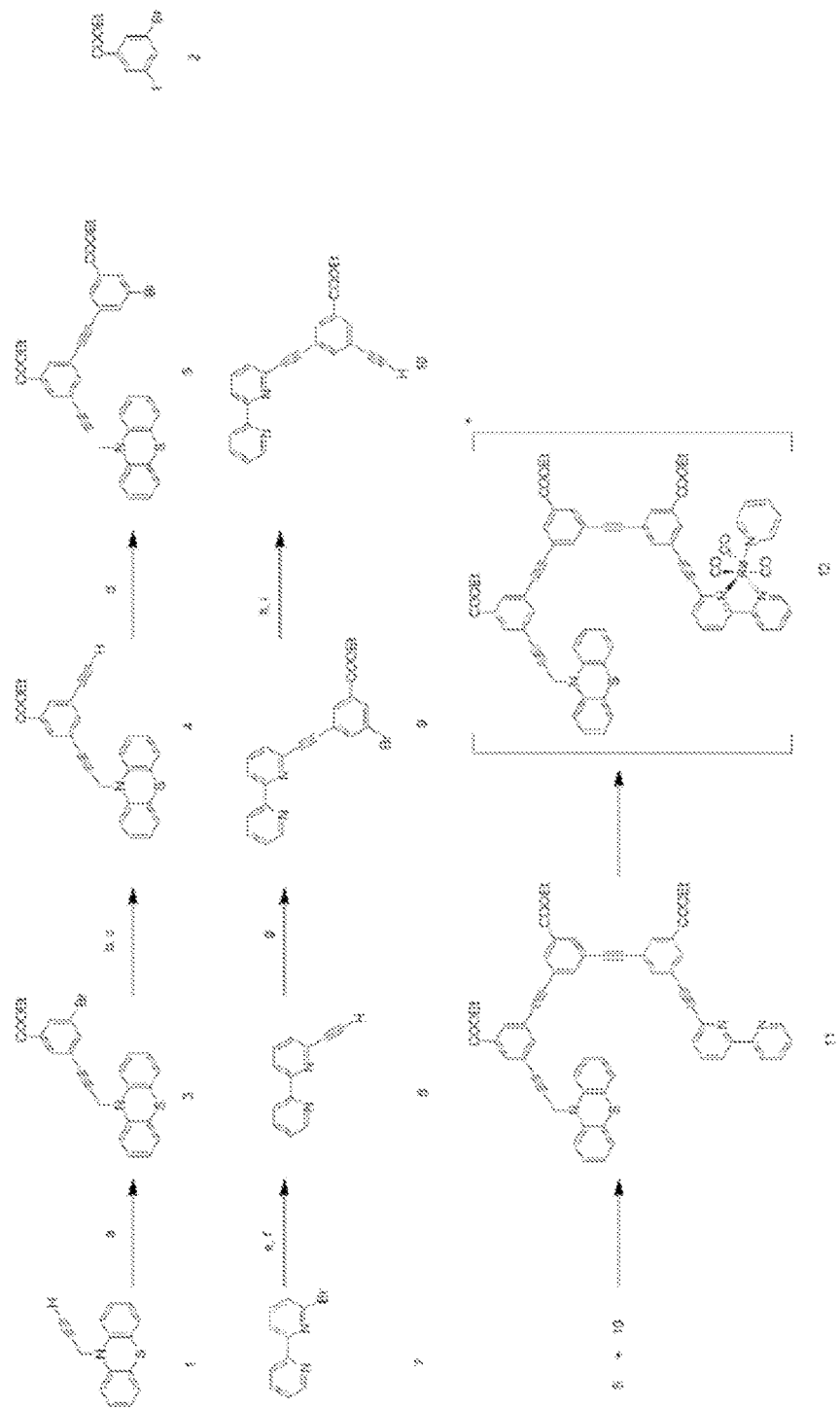
FIG. 8 depicts Synthesis of D-B-A complex (12)$^a$. In brief, in one embodiment, the reagents comprise Reagents and conditions: a) propargyl bromide, K2CO3, toluene, reflux. b) 2, bis(triphenylphosphine)palladium(II) dichloride, ZnCl2, THF, Et3N, 100° C. c) TBAF, THF, room temperature. d) 2, bis(triphenylphosphine)palladium(II) dichloride, ZnCl2, THF, Et3N, 100° C. e) trimethylsilyl aceytlene, bis(triphenylphosphine)palladium(II) dichloride, ZnCl2, THF, Et3N, 100° C. f) TBAF, THF, room temperature. g) 2, bis(triphenylphosphine)palladium(II) dichloride, ZnCl2, THF, Et3N, 100° C. h) trimethylsilylaceytlene, bis(triphenylphosphine)palladium(II) dichloride, ZnCl2, THF, Et3N, 100° C. i) TBAF, THF, room temperature. j) bis(triphenylphosphine)palladium(II) dichloride, ZnCl2, THF, Et3N, 100° C. k) Re(CO)5Cl, toluene, reflux. l) AgClO4, pyridine, CH3OH, toluene, 50° C.

The development of a synthetic strategy for the D-B-A complex involves the construction of a donor-bridge ligand (D-B) (11) that covalently binds to the acceptor moiety to form the final complex (12) (Scheme 1; FIG. 8). The donor is 10-(prop-2-yn-1-yl)-10H-phenothiazine (1), the acceptor is based on rhenium (I) tricarbonyl chloride diimine complex, and the bridge is composed of three phenylene-ethynylene units. The D-B ligand features a terminal bipyridine, capable of binding strongly to rhenium, eliminating the need for synthesis of D-B ligand in large quantities. 11 was constructed in a stepwise approach using zinc-mediated, palladium-catalyzed cross-coupling reactions in a microwave reactor and protecting group strategies. More precisely, the synthesis of 11 begins with the selective coupling of the donor (1) to 3-bromo-5-iodobenzoate (2). Both 1 and 2 were prepared according to established protocols. The resulting compound (3) was coupled with trimethylsilyl acetylene and subsequent removal of trimethylsilyl group was accomplished by treatment with tetrabutylammonium fluoride (TBAF) to afford ethynylene-terminated 4. The alkynyl group of 4 was then coupled to 2 to give phenothiazine-terminated 5 with a bromo functionality. Assembly of 11 requires an ethynylene-terminated bipyridine connected to a phenylene-ethynylene unit (10) be linked to 5. Synthesis of 10 begins with commercial 6-bromo-2,2'-bipyridine, which was acetylated and deprotected before reaction with 2 to yield a bromo-bipyridine derivative attached to a phenylene-ethynylene unit (9). Acetylation of 9 followed by deprotection with TBAF gave 10. Subsequent cross-coupling of 10 to 5 yielded the D-B ligand (11). The D-B-A complex (12) was obtained by metalating 11 with rhenium (I) pentacarbonyl chloride using general metalation procedures followed by reacting the resulting compound with pyridine in the presence of silver perchlorate in the dark.

The complex, [Re(CO)3(bpy)(py)]+(bpy=2,2'-bipyridine, py=pyridine), was also prepared using established protocols.

Absorption Properties of the D-B-A Complex

The absorption spectrum of the D-B-A complex solution in dichloromethane solution display three principle features (FIG. 1a). The intense, high energy absorptions (260-320 nm) in the D-B-A complex are attributed to ligand-based $\pi$-$\pi$* transitions. This band is also present in the spectrum of 6-ethynyl-2,2'-bipyridine. There is a broad band centered at 255 nm that is characteristic of phenothiazine. This band is absent in [Re(CO)3(bpy)(py)]+. The broad feature between 340 and 390 nm is attributed to metal-to-ligand charge transfer. This band is absent in the absorption spectrum of the D-B ligand. Absorption bands associated with the bridge are not observed; however, cross-coupling of the 10-(prop-2-yn-1-yl)-10H-phenothiazine to the 3-bromo-5-iodobenzoate results in broadening of the band centered at 255 nm.

Emission Properties of the D-B-A Complex

Figures 6A, 6B:
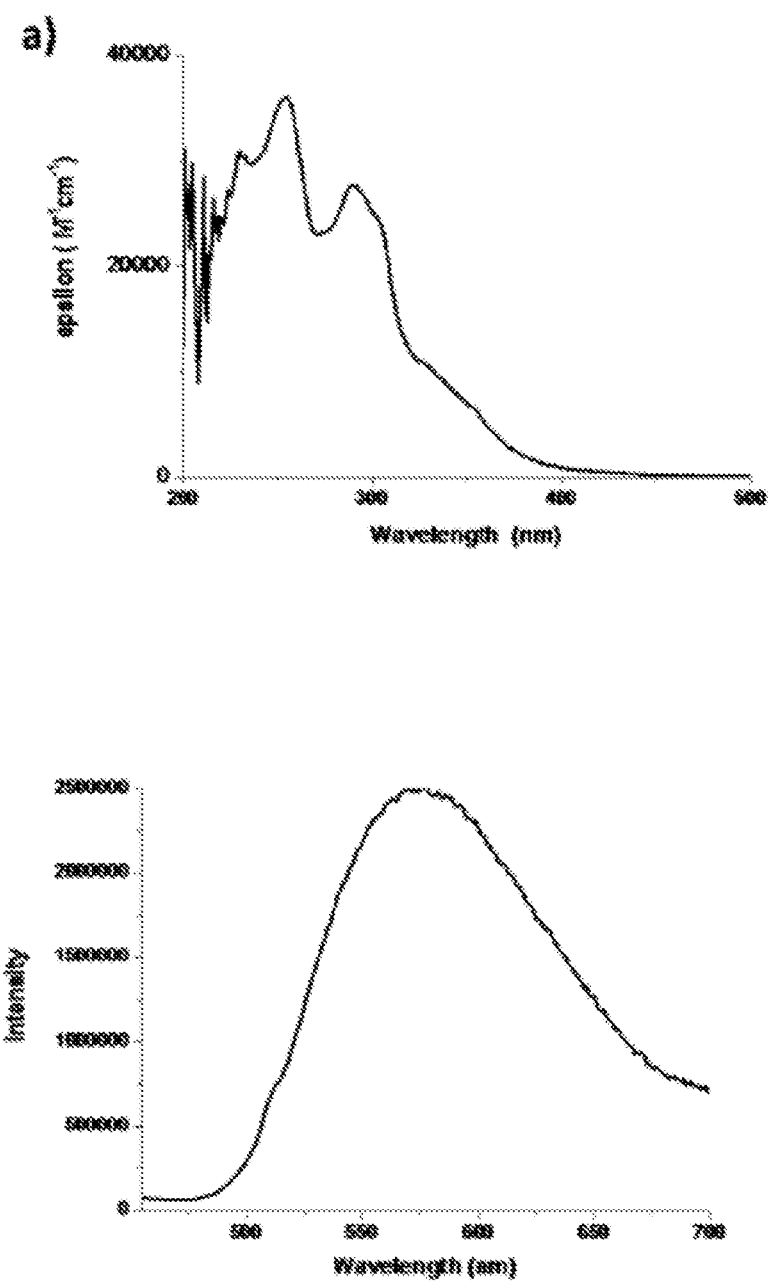
FIGS. 6A-6B depict the a) absorption and b) steady-state emission spectra of 15 µM D-B-A complex.
Figures 7A, 7B:
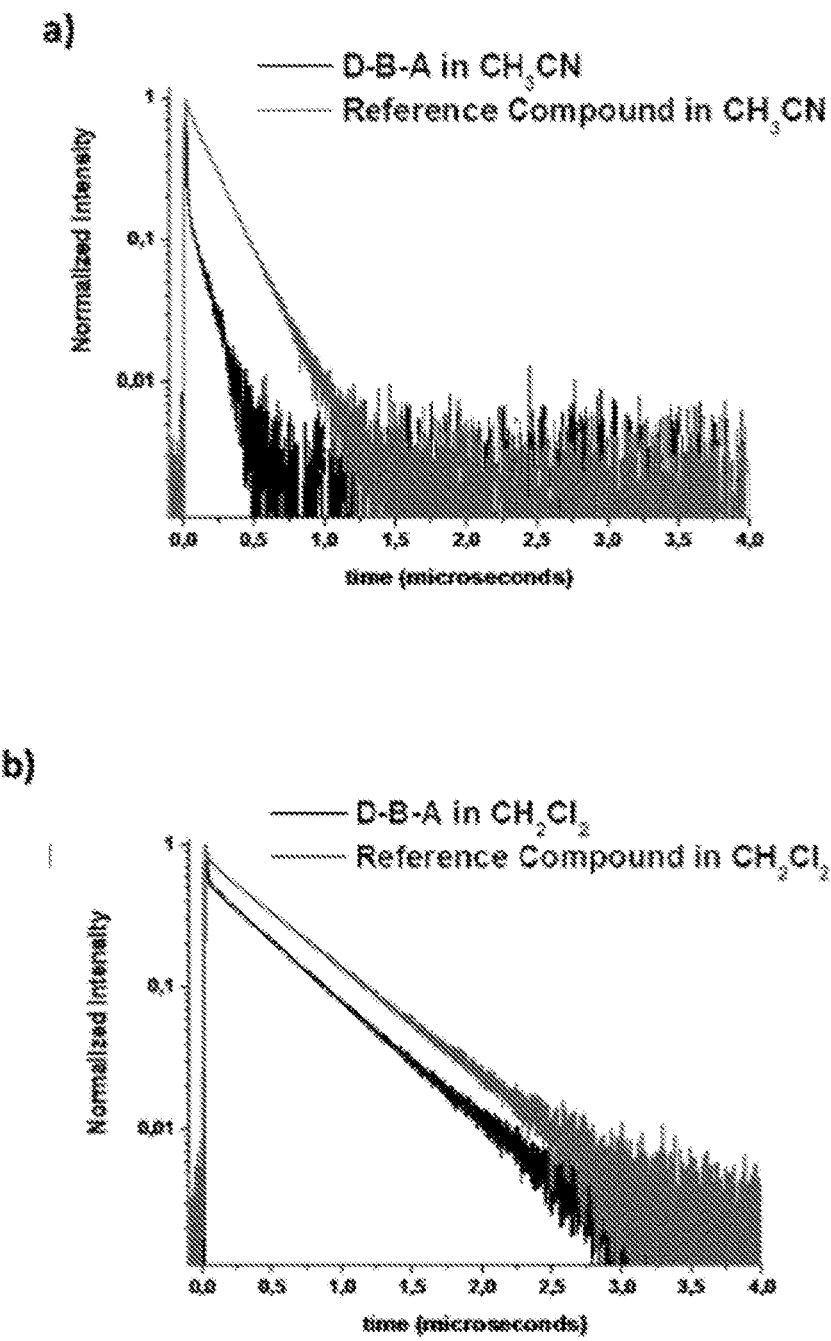
FIGS. 7A-7B depict time-resolved emission spectra of D-B-A complex and [Re(CO)3(bpy)(py)]+ in CH2Cl2.

The steady-state emission spectrum of the D-B-A complex in dichloromethane solution has a broad band centered at 575 nm (FIG. 6B), which is characteristic of metal-to-ligand charge transfer (MLCT) emission of similar complexes.

Time-resolved emission spectroscopy was used to characterize the MLCT excited state of the D-B-A complex. Luminescence decay kinetics were recorded in degassed dichloromethane. The D-B-A complex was excited at 355 nm with an 8-ns laser pulse and luminescence was monitored at 560 nm. The luminescence showed monoexponetial decay with a lifetime of 500 ns. For comparison, the MLCT lifetime of the reference complex, [Re(CO)3(bpy)(py)]+, determined under identical experimental conditions, is 550 ns.

The decrease in luminescence lifetime is attributed to PTZ→*Re charge transfer. A signal corresponding to the PTZ radical cation (PTZ+•) was not observed in transient absorption spectra collected at 525 nm. This is likely the result of rapid charge recombination, which prevents a significant quantity of the charge separated state from accumulating. A photolyzed sample containing the D-B-A complex and an irreversible oxidant was shown by EPR to generate organic radicals.

Excited-State Electron Transfer

Three electron transfer quenching mechanisms may contribute to the shorter lifetimes and lower emission quantum yields of the D-B-A complex: (1) intramolecular electron transfer, (2) static electron transfer, and (3) dynamic electron transfer (Scheme 2). Both static and dynamic electron transfer are intermolecular processes. Static quenching implies a pre-associated complex with two or more D-B-A molecules arranged such that rapid electron transfer between two subunits occurs. Finally, dynamic electron transfer describes a diffusion-controlled collisional quenching mechanism.

Intramolecular ET describes electronic coupling of the excited-state rhenium and phenothiazine moieties within the same D-B-A complex. ET may proceed through the extended π-framework of the bridge. Alternatively, the flexible linker may permit the through-space distance between donor and acceptor to become quite close, favoring solvent-mediated electron transfer.

Scheme 2.

$$D\text{-}B\text{-}A^* \to D\text{+-}B\text{-}A\text{-} \qquad (1)$$

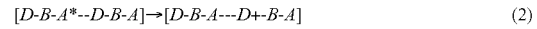

$$[D\text{-}B\text{-}A^*\text{--}D\text{-}B\text{-}A] \to [D\text{-}B\text{-}A\text{---}D\text{+-}B\text{-}A] \qquad (2)$$

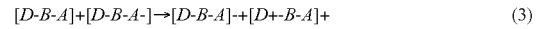

$$[D\text{-}B\text{-}A] + [D\text{-}B\text{-}A\text{-}] \to [D\text{-}B\text{-}A] + [D\text{+-}B\text{-}A] + \qquad (3)$$

D-B-A complexes containing meta-phenylene ethynylene bridges have been shown to aggregate under certain conditions. Self-association often leads to enhanced quenching, due to the formation of aggregates with short intermolecular donor-acceptor distances. While the monoexponetial decay of the luminescence suggests only monomeric species in solution, it is possible that self-association promotes rapid intermolecular ET whose decay kinetics exceed the time resolution of our instruments. To verify that no aggregation is occurring in the D-B-A complex prepared in this work, a combination of UV-vis, steady-state fluorescence, electron paramagnetic resonance (EPR), and NMRspectroscopies were employed. NMR spectra of the D-B-A complex in dichloromethane solution of concentrations ranging from 1.35 mM to 0.13 mM did not exhibit significant change in the position of resonances, and no additional resonances were observed as concentration was varied. Absorption and emission spectra of the D-B-A complex at concentrations varying from 32 µM to 1.51 mM did not exhibit significant change in peak position, and increasing concentration does not produce additional spectral features. These results suggest that there is no aggregation.

While the rate of intramolecular ET is concentration independent, intermolecular quenching processes vary predictably with concentration. As such, it is possible to separate the two quenching mechanisms and obtain rate constants for each. Time-resolved luminescence measurements at a series of D-B-A concentrations allow a second order intermolecular quenching rate to be determined. As the concentration was increased, shorter lifetimes were recorded in both dichloromethane and acetonitrile. From these data, a dynamic quenching rate (kq) of $1.1 \times 10^6$ $M^{-1}$ $s^{-1}$ and was obtained.

From this analysis, the lifetime of the complex in the absence of intermolecular quenching, $\tau_0$, was found to be 530 ns. This lifetime includes both the natural decay of the photoexcited rhenium as well as quenching through intramolecular electron transfer. From these data, an intramolecular ET rate of $6 \times 10^4$ $s^{-1}$ and quantum yield of 3% were calculated for the D-B-A complex. As the difference in lifetime of the D-B-A and model complex is quite small, these values should be considered upper bounds.

Electron transfer experiments on oligo(p-phenylene ethynylene) donor-bridge-acceptor complexes have provided exponential distance decay ($\beta$) values of 0.3-0.6 Å-1. 39,56 These values coupled with an estimated intermolecular ET rate of $1.6 \times 10^{11}$ $s^{-1}$ for [Re(CO)3(bpy)(py)]+ and PTZ held at contact, predict an intramolecular ET rate for the D-B-A complex to be between $8 \times 10^3$ $s^{-1}$ and $4 \times 10^6$ $s^{-1}$. These values suggest that meaningful long-range intramolecular ET may occur in these D-B-A systems.

Intramolecular ET may also proceed through a through-space coupling mechanism.57,58 Unlike the rigid oligo (para-phenylene ethynylene) bridged complexes, the meta-linked species studied here is much more flexible, allowing the through-space donor-acceptor distance to become quite small. Molecular modeling suggests the D-B-A complex can easily fold into a U-shape, placing donor and acceptor moieties within 10 Å. Tunneling through a non-covalent medium typically displays sharply higher $\beta$ values; however, may be competitive with through-bond electron transfer over short distances. Electron transfer studies in frozen glasses have shown $\beta$ values of certain organic solvents to be in the range of 1.2 to 1.6 Å-1. If $\beta$ values in this range are used, the through-solvent intramolecular ET rate is predicted to fall between $10^4$ and $10^6$ $s^{-1}$, which is competitive with calculated through-bond tunneling rates.

Conclusions

A new D-B-A complex has been synthesized based on the methods disclosed herein, where a rhenium tricarbonyl electron acceptor is linked via an oligo-m-phenylene-ethynylene bridge to a phenothiazine donor. A combination of transient absorption, emission, and EPR spectroscopy was employed to investigate the photoinduced electron transfer properties of the D-B-A complex. These studies indicate the D-B-A complex undergoes photoinduced ET. Theoretical work suggests that both through-bond and through-space electron tunneling are capable of promoting intramolecular electron transfer in these systems.

Example 3

As discussed above, several embodiments of the present invention relate to the use of light to control neural activity by generation and administration of photovoltaic nano-switches (PVNs). In several embodiments, the PVNs disclosed herein are suitable for embedding in the outer face of the neural membrane and, upon illumination, reversibly alter electrical activity of the cells in which they are embedded. Advantageously, PVNs as disclosed herein operate, in several embodiments, without the need to express foreign proteins and PVNs function at visible wavelengths and at near-ambient light intensities. Thus, in several embodiments, the PVNs not only enable further development of the knowledge base related to electrical signaling in neural circuits and neuroendocrine tissues, as well as in the retina of animal models for photoreceptor degeneration, but also are positioned to reduce the major health burden of heretofore, untreatable adult blindness, by providing a new treatment specifically for photoreceptor degeneration diseases such as retinitis pigmentosa, as well as the more prevalent end-stage age-related macular degeneration (among other maladies). Further, in several embodiments, the methods and compositions disclosed herein provide a functional bridge that provides a tunable mechanism for light-based signaling between man-made devices and human tissues, possibly overcoming the limitations of metal and polymer-based electrodes, with far-reaching impact on therapies for neurological conditions ranging from neuromuscular paralysis to epilepsy.

As discussed above, experimental data have been generated that demonstrate that a PVN based on ruthenium bipyridine ("Rubpy") inserts into cell membranes and, upon illumination, triggers action potential firing in cultured excitable cells. Additionally, experimental data discussed in more detail below, demonstrates that injection of PVNs into eyes of blind rats confers visually induced electrical activity in the superior colliculus. In several embodiments, the light induces an electrical dipole in the PVNs, depolarizes the cell membrane and thereby activates neuronal firing. These data are an important indicator that restoration of vision using the methods and compositions disclosed herein is possible.

Loss of photoreceptors due to retinal degenerative diseases such as retinitis pigmentosa (RP) and age-related macular degeneration (AMD) are some of the most common acquired causes of adult blindness. Not only is there presently no cure, there are few ameliorative treatments. Although photoreceptors are lost as a result of those diseases (among other maladies), a significant number of the inner retinal neurons survive and remain capable of delivering visual information to the brain. Advantageously, certain embodiments of the methods disclosed herein, involve the delivery of PVNs to these surviving neurons, which enables significant advances in the treatment of late-stage AMD and RP (among other maladies caused, at least in part, by reduced or failed neurotransmission). Advantageously, PVNs disclosed herein have photophysical properties that are readily customized. They may also provide heightened visual acuity as compared to other retinal treatments, as the light-activated signaling unit is individual neurons, rather than groups of neurons near an electrode. PVNs are also less invasive than most retinal implants, do not require concomitant gene therapy, and they function using noncytotoxic excitation wavelengths.

While, the PVN compositions disclosed herein are advantageously tunable to fit the needs of a particular patient population or disease population, there are certain "ideal" properties shared by the PVNs disclosed herein. As discussed above, the PVNs embed in the neural plasma membrane, conferring light-inducible changes in action potential firing rate. The molecules have the property that they generate an electrical dipole upon absorbing light. Ideally, the PVNs are able to absorb light at visible wavelengths at ambient light intensity. The resultant light-induced electrical dipole serves to activate voltage-gated ion channels, such as the voltage-gated sodium channel or calcium channels. A PVN anchored on the outer membrane surface that generates a negative surface charge upon illumination can alter the gating of a plasma membrane voltage-gated ion channel in the same direction as membrane depolarization. The duration of the light-induced dipole is preferably sufficiently long to activate sodium channels (e.g., $\geq 100$ μs), but not so long as to cause irreversible channel inactivation or excitotoxicity ($\leq 10$-$100$ ms). Mechanistically, the electrical dipole can activate voltage-gated ion channels either indirectly (e.g., by charging the membrane capacitor) or directly (e.g., by interacting with the voltage-sensor domain of the targeted ion channel). Also, because the molecules act from the outside of the cell, cell-specific targeting of the PVNs is accomplished, in several embodiments, through selective binding to neuronal surface markers and, in still additional embodiments, to specific ion channels. Depending on the embodiment, targeting can be accomplished using, for example, highly specific peptides, (e.g., modified scorpion toxins) or high-affinity peptides, such as those identified by phage or mRNA display. Additionally, PVNS should exhibit little to no toxicity and are preferably non-immunogenic.

Other approaches exist in the neurophotonics field, although they exhibit significant shortcomings when compared to the PVN compositions and methods disclosed herein. Table 1 compares three approaches, including the PVN approach disclosed herein. Optogenetic approaches involve heterologous expression of light-responsive proteins in the cell membrane. Among the most extensively studied families of light-gated proteins are microbial opsin-based ion channels and pumps, for which light typically triggers the conformational change of the light-sensing chromophore (all-trans retinal), thereby opening the ion flow pathway and transporting the ions across the membrane, resulting in the depolarization or hyperpolarization of the cell membrane. Following the introduction of wildtype light-sensitive proteins such as blue light-sensitive channelrhodopsin (ChR), yellow light-sensitive halorhodopsin (NpHR) and green light-sensitive bacteriorhodopsin (BR), a multitude of variants were created to yield shifted action spectra, improved light sensitivity and modified kinetics. In comparison with endogenous ion channels found in retinal neurons, microbial opsin-based channels generally produce substantially smaller single channel current, thus requiring over-expression of the protein on the membrane and extra high illumination intensity in order to provide sufficient control of neural activity. The commonly used light intensity in optogenetics varies from tens to hundreds of $mW/mm^2$, which, in the long term, may cause unwanted thermal effects in biological tissues. In addition, the safety concern about the delivery and expression of foreign genes remains a major hurdle for the ultimate application of optogenetics in humans. Alternative strategies for engineering light control of retinal neurons include use of small-molecule azobenzene-based photoswitches that undergo photoisomerization from a trans (linear, relaxed) state to a cis (bent) state upon UV illumination, and undergo the reverse conformation change upon longer wavelength illumination. The azobenzene moiety is covalently attached either to tetraethylammonium (a potassium channel blocker) or to ion channel ligands (or ligand derivatives) in order to enable light to be used to gate potassium channels or nicotinic acetylcholine, GABA or glutamate channels. Though successfully demonstrated to restore visual percepts in blind rodents, the need for UV illumination and the difficulty in tuning the absorption spectrum towards visible wavelength in many cases pose obstacles to clinical translation of such UV-sensitive photochemistry tools.

TABLE 1

Comparison of approaches to impart light responsiveness

| Property | Photovoltaic Nano-switches | Azobenzene Photoswitches | Channelrhodopsin/ Halorhodopsin |
|---|---|---|---|
| (1) Excitation wavelength | $\geq 450$ nm | 340-380 nm | 450-650 nm |
| (2) Intensity of light used (order of magnitude) | ~1-20 $\mu W/mm^2$ | ~100-500 $\mu W/mm^2$ | 1-300 $mW/mm^2$ |
| (3) Second wavelength to reverse activity | No | Yes | No |
| (4) Genetic manipulation | No | No | Yes |
| (5) In vitro evidence for light-induced activation of cellular electrical activity | Yes | Yes | Yes |
| (6) Evidence of improving visual behavior in animal models of photoreceptor loss | Yes | Yes | Yes |

In contrast to the approaches above, several embodiments of the invention disclosed herein confer light sensitivity on the neurons surviving in a photoreceptor-degenerate retina by delivery of PVNs into the eye. The approaches disclosed herein advantageously obviate the need for foreign gene expression or cytotoxic ultraviolet light activation. As such, the approaches disclosed herein, in several embodiments, can aid in restoration of vision, at least in part, for patients at advanced stages of AMD and RP while offering greater visual acuity than current epi- or sub-retinal implants, reduced invasiveness, no requirement for gene therapy, and functionality at non-cytotoxic excitation wavelengths. Moreover, PVNs as disclosed herein offer, in several embodiments, solutions to the limitations of metal and polymer-based electrodes (e.g., short functional lifetimes due to electrochemical degradation and due to foreign-body response). This enables the PVNs to be extended to the treatment of neurological conditions ranging from neuromuscular paralysis to epilepsy. PVNs offer bi-directional modulation of the membrane potential of a cell in a single biophotonic switch, which affords the ability to both activate and inhibit the action potential firing of the illuminated cells with the same molecule. This imparts clinical flexibility as well as the ability to establish, in combination with high-resolution optical system for multi-loci photo-stimulation, a high-throughput platform for fine-grained analysis of a variety of neural networks. By changing the spatial and temporal parameters of the pixels, various illumination patterns can be generated that allows extensive applications, for example, in the mapping of neural circuits. Moreover, PVNs can be used in the study of any electrically excitable cell, including, for example, cardiomyocytes, smooth muscle cells, neuroendocrine cells, and certain glial and cancer cells.

Figure 13:
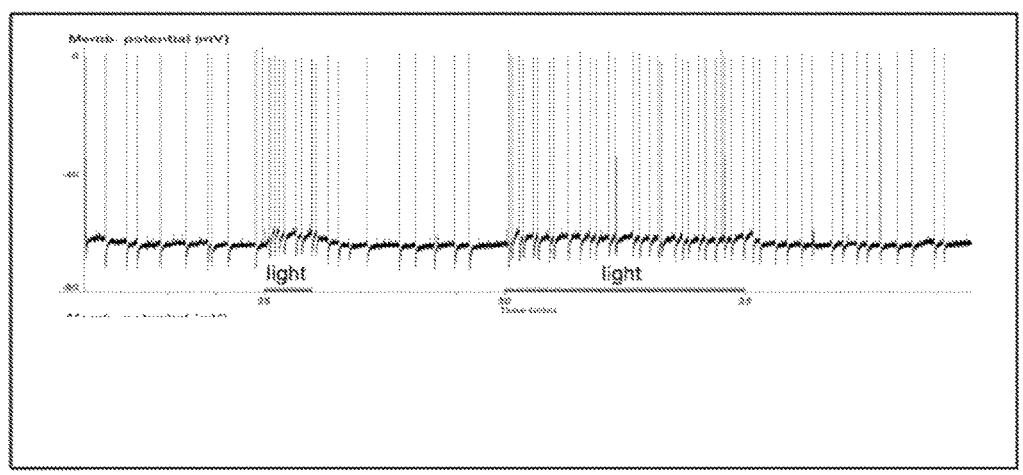
FIG. 13 depicts data from leech ganglion neurons that showed light-induced increases in action potential firing with Rubpy-C17.
Figure 14:
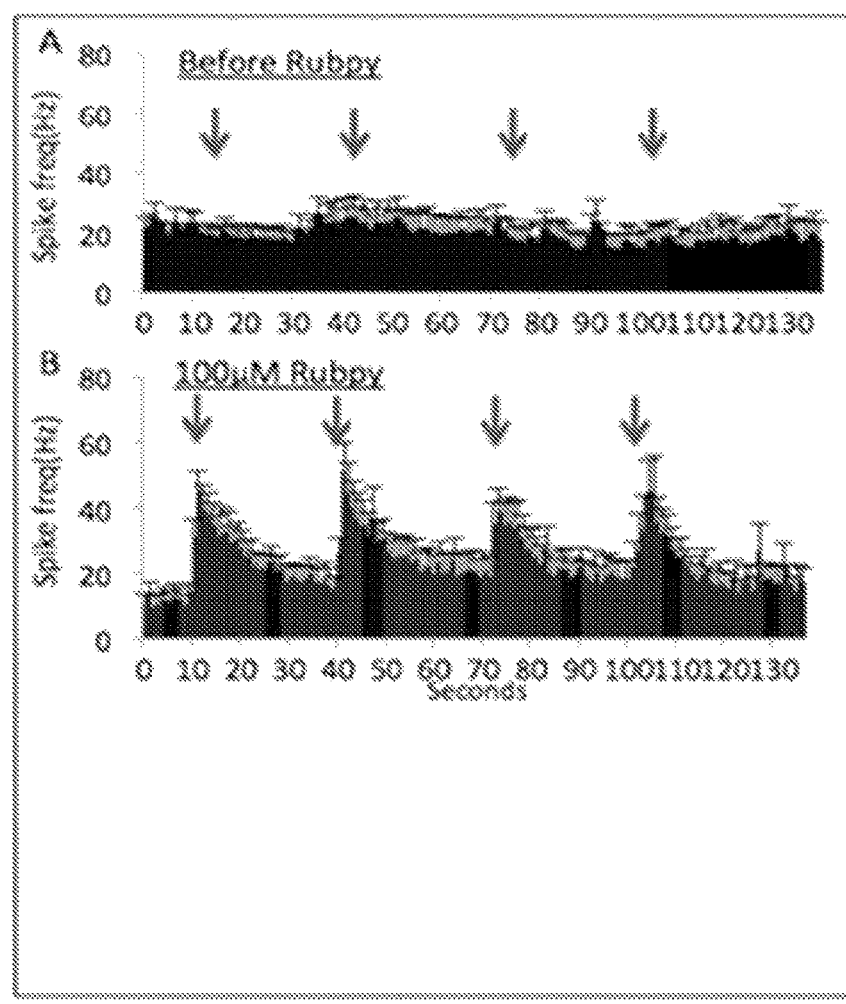
FIGS. 14A-14B depicts data from whole-mount retinas from RCS rats. The data show binned data from 11 electrodes. Each bin represents the frequency of spikes for 1 second. Before Rubby treatment (14A), illumination at 480 nm elicited minimal change in spike frequency. After treatment (100 micromolar for 30 minutes) spike frequency increased. Downward arrows mark the time of 100 ms (1st) and 1 second (2nd to fourth) light stimuli.

The experimental results discussed above demonstrated that Rubpy-C17 inserts into cell membranes where it luminesces, confirming membrane localization and illumination of Rubpy-C17-treated cells results in depolarization, action potential firing, and secretion in the presence of bath ascorbate, but hyperpolarization in the presence of bath ferricyanide. The direction of membrane potential change depends on the redox state of the environment. The vitreous of the eye and the extracellular fluid of the brain are reducing environments, containing ascorbate at ~2 mM concentration. Additional experiments demonstrated that Rubpy-C17 treatment of leech neurons in ex vivo ganglia (FIG. 13) and retinal neurons in wholemount photoreceptor-degenerate retina (FIG. 14) respond to illumination by firing action potentials.

Figure 15:
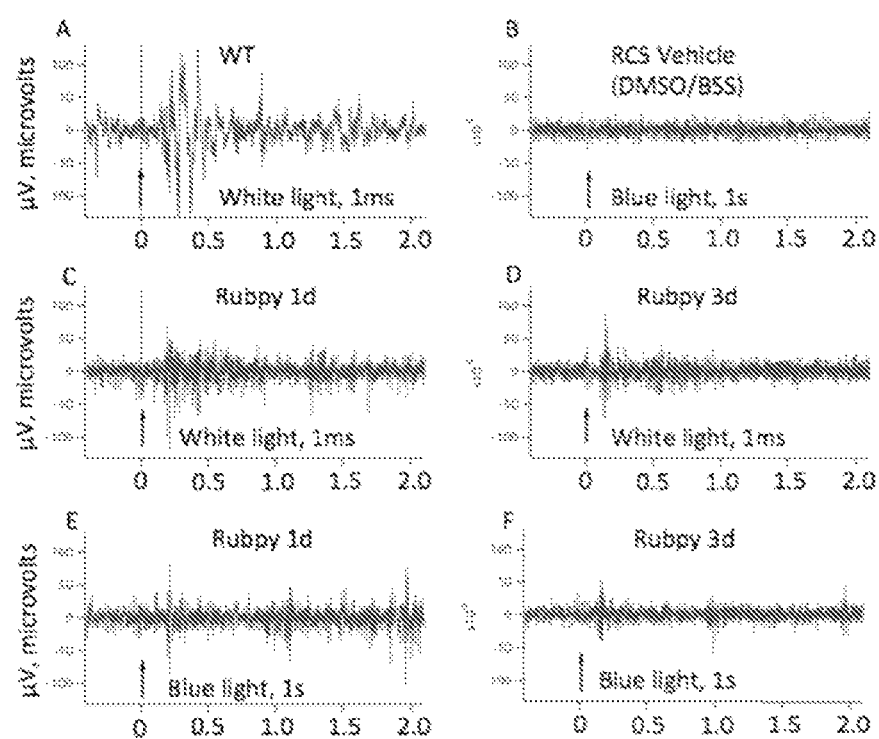
FIGS. 15A-15F depict extracellular recording from the superior colliculus of wild type of RCS rats.
Figure 16:
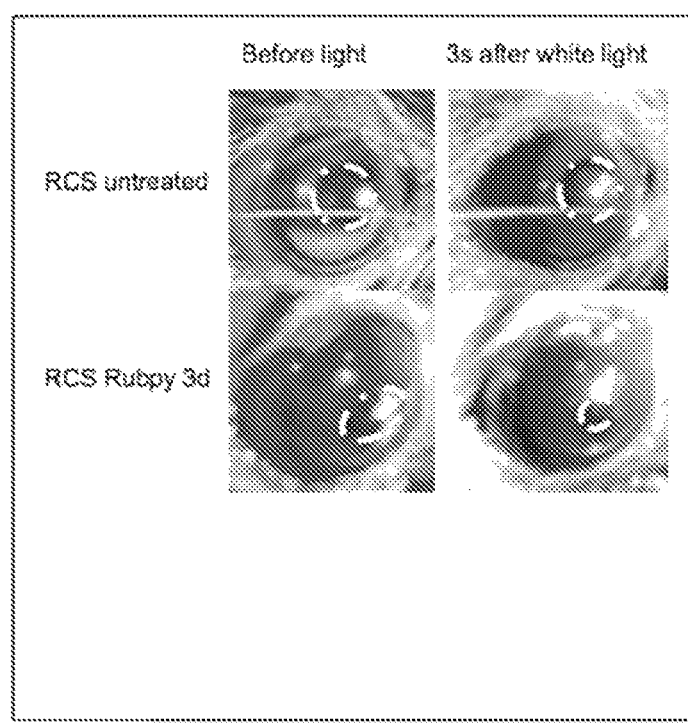
FIG. 16 depicts the papillary light response in RCS rats. The pupil constricts in the left eye previously injected with Rubpy-C17 (1 mM in 5 microliters) but not in the non-injected right eye in an RCS rat at 9 months of age.

In a demonstration of the efficacy of PVNs in vivo, intravitreal injections of Rubpy-C17 (final concentration of 100 µM) were made into the eyes of confirmed-blind Royal College of Surgeon (RCS) rats. 30 minutes later, a craniotomy was performed on the anesthetized rat to expose the superior colliculus. Illumination of the eye injected with Rubpy-C17, but not with a sham solution, elicited reproducible and stereotypical electrical activity in extracellular field recording (FIG. 15). This finding was reproduced in 3 of 3 RCS rats injected with Rubpy-C17, and in 2 of 2 control (sham injection) RCS rats. In addition, a vigorous pupillary light reflex was observed in the Rubpy-C17 injected eye (<3 sec), but not in the non-injected eye (FIG. 16). Finally, preliminary histology of the retina at 3 days after injection reveals no evidence of retinal cell death or white blood cell infiltrates, thus confirming limited toxicity of the PVN at this timepoint.

Optimization of Electrochemical and Photophysical Properties of PVNs to Enhance Activity and Reduce Potential Side Effects The data presented herein suggest that the light-induced membrane potential change in Rubpy-treated cells and tissues arises from the inter-molecular electron transfer between a sacrificial redox molecule and the membrane-anchored Rubpy-C17 (to be contrasted with intra-molecular transfer, see below). The direction of the electron transfer depends on the relative redox potentials of Rubpy-C17 and redox-active molecules in the environment. Interestingly, the rate of membrane potential change mediated by PVNs is relatively slow (e.g., ~40-second time scale) when studied in single cells, whereas it is much faster (e.g., ~100 ms time scale) in in vivo studies in which PVNs are injected into the eyes of blind rats. In some cases, the redox environment of single cells is very different from the case of complex tissue environment of the intact eye. Thus, in several embodiments, Rubpy analogues having a range of redox potentials are generated. For example, ruthenium(II) bipyridine transition metal complexes are highly tunable to the redox properties of specific biological systems. Thus, in several embodiments, the Rubpy-C17 can be modified in order to optimize redox potential, quantum yield, excited state lifetimes and electron transfer rates for efficient membrane depolarization.

The ruthenium metal center of the parent molecule tris (bipyridine)ruthenium(II) ([Ru(bpy)$_3$]$^{2\pm}$, when excited with visible light to attain the excited state, can be either reduced or oxidized, resulting in a Ru(I) or Ru(III) species, respectively. Modification of the bipyridine ligand (e.g. by adding specific electron-donating or -withdrawing substituents at specific locations on the bipyridine ligands) biases the reactivity of the photoexcited complex (as well as other photophysical properties) and the subsequent formation of Ru(I) or Ru(III) species. Thus, overall charge and reduction potential are two characteristics of the Rubpy-C17 that can be systematically varied, depending on the embodiment, to enhance for mechanistic understanding, further molecular artificial retina design, and tailor the PVN to a particular patient and/or disease.

In several embodiments, photoexcitable ruthenium complexes capable of intra-molecular electron transfer with multiple covalently tethered electron acceptors are used, as they are thought to be most effective at accumulating localized negative charge in a reversible, productive manner (the donor-acceptor molecules are named "DAsies"). Similar to tuning the reduction potential by introducing electron-donating or electron-withdrawing groups to the bipyridine ligands, conjugating different electron-accepting groups (e.g. methyl viologen or benzoquinone) to the bipyridine ligands at a distance enables, in several embodiments, adjusting the rate of directed electron transfer. By varying the number of intra-molecular electron acceptors at appropriate distances from the ruthenium metal center to facilitate fast forward electron transfer and slow back electron transfer, this precise temporal and spatial control serving to facilitate use of molecular artificial retinas with reduced side effects.

PVNs Confer Light-Sensitivity to Neurons

As the results above demonstrate, ex vivo tissues such as leech ganglia and wholemount retina from blind RCS rats (a photoreceptor-degenerate model), when bathed in PVN solution, also exhibit light-induced action potential firing. These models are readily amenable to testing the various PVN embodiments contemplated, in particular to quantify the illumination intensity required for a change in action potential frequency, the latency for a response, and the reversibility of the changed rate of firing for the set of Rubpy analogues.

Further Corroborative Studies Related to PVN Conferring Light Sensitivity to Neurons To further examine the mechanism of action, the action of PVN in giant unilamellar vesicles (GUVs), cell-sized artificial liposomes, will be studied. Because they do not contain endogenous ion channels or other cell membrane proteins, these liposomes will allow examination of whether light-induced membrane potential changes occur even in the absence of membrane proteins. This is important for ruling out the role of channels in the depolarization, and ruling out the role of membrane proteins as electron acceptors that maintain membrane depolarization. In addition, the size of GUVs can be controlled and therefore, the input impedance, which will allow testing for the role of membrane damage/perforation by choosing to study smaller GUVs, having higher impedances so that even small currents (small membrane perforations) are detectable.

The time course of membrane depolarization is relatively slow and slow recovery of resting membrane potential, according to the data above. However, the time to respond to illumination and the recovery from light-triggered increase in activity is much more rapid as studies moved from single cells (10 s of seconds) to intact neural network (1-2 seconds) and in vivo (100 ms) studies. Two alternative hypotheses to explain the apparent discrepancy in the temporal behavior are (1) the slow membrane potential change, followed by plateau depolarization may be an artifact of the method (patch clamp) used to measure single-cell potential changes, or (2) the membrane potential remains persistently depolarized because the Rubpy complex transfers its electron to a membrane-localized electron acceptor molecule, which serves to keep the outer face of the membrane negatively charged (e.g., it stays depolarized). Thus, in several embodiments, the PVNs will employ molecules with different chemistry—for example, some iridium complexes display much faster light-induced membrane depolarizations. Moreover, PVNs may, in several embodiments, comprise different baseline charge. For example, the nanophotoswitches may insert into the membrane and with a particular baseline charge (sufficient to avoid the molecules' flipping across the membrane) to reduce the threshold for changes in electrical activity. Additionally, the nanophotoswitches can be coupled to voltage-gated ion channels. As discussed above, targeting can be achieved through high-affinity peptides derived from scorpion toxins, antibodies, or phage display, to the use of polyunsaturated fatty-acid (PUFA)-like membrane anchors, which have recently been shown to associate with voltage-gated ion channels in the hydrophobic membrane domain.

Further, the devices disclosed herein address the aspect of light-amplified image projection onto retina. Ambient photon flux may be insufficient for significant or fast light-activation. An intraocular camera with image display projected onto the retina or a headmounted visor, with similar projection onto the retina. Such devices would offer the ability to match wavelength and photon flux of the displayed image to the requirements of the nanophotoswitch-treated retina (see e.g., FIG. 9).

To these hypotheses, single-cell studies will be repeated using extracellular recording to rule out the artifact from patch clamping. By studying the action of the PVN in GUVs, it will be determined whether a membrane component serves as an electron acceptor to keep the membrane depolarized. The major experiments to test the mechanism are discussed below.

Experiment 1. Single-Cell Mechanism—Patch Clamp

Repeat single-cell studies using patch clamp, including whole-cell and perforated patch clamp in cultured, single non-excitable cells and neuroendocrine cells will be performed. For each of the Rubpy analogues, cells will be incubated with the Rubpy analogue at 1 µM (all the analogues are synthesized with a. single C17 aliphatic chain, and at this concentration the parent complex Rubpy-C17 adequately stains the cell membrane, giving luminescence that can be observed). Electrical activity will be monitored and the latency to membrane potential change, action potential firing upon illumination, and the reproducibility of repeated rounds of illumination to trigger action potential firing will be determined.

Experiment 2. Single-Cell Mechanism—Extracellular Recording

Mouse adrenal chromaffin cells will be grown on multi-electrode arrays (MEAs) and extracellular recording will be performed. Cells will be perfused with 1 µM Rubpy analogue solution for 10 minutes and washed with PVN-free solution for 10 minutes before recording is performed. Light-triggered change in action potential firing rate will be monitored before and after PVN treatment. Cells will be exposed to repeated episodes of illumination and dark periods at the appropriate wavelength with intervals between pulses from 6-60 s and intensities from 1-20 µW/mm$^2$. Extracellular recording allows measurement from intact cells, which complements the patch clamp method, offering an alternative approach to screen PVNs and examine the mechanism.

Experiment 3. Giant Unilamellar Vesicle Assay

GUVs of diameter ~10-20 µm, will be generated using standard electroformation protocols. The lipid composition will be chosen to resemble the plasma membrane. The GUV will be bathed with 10 µM Rubpy-C17 for 10 minutes, and then washed with Rubpy-free buffered salt solution containing 2 mM ascorbate or 200 mM potassium ferricyanide for another 10 minutes. Standard perforated-patch or whole-cell configuration of patch clamp will be used to record membrane potential in current clamp mode, viewing the GUV's under a standard fluorescence microscope, with illumination provided by a white-light LED via the epi-illumination port.

Experiment 4. Wholemount Retina, Temporal and Spatial Studies

The wholemount retina from RCS rats of ≥9 months of age (blind) will be placed with retinal ganglion cell (RGC)— side-down on standard MEA, treated with Rubpy analogue at 10 µM, and illuminated globally to activate the inner retina. Illumination will be sourced from an LED at 1-20 µW/mm$^2$. In one set of experiments, the duration of the light stimulus and the intensity will be varied systematically. In another experiment, light stimuli will be applied in triplicate, having progressively shorter inter-pulse intervals, in order to assess both the speed of response and the reversibility of the light-induced effect. The change in spike frequency and the time from onset of illumination to an increase in action potential firing frequency (latency) will be quantified.

The spatial resolution will be determined by illuminating the wholemount retina with a focal light aiming to excite only one to few RGCs and the spatial resolution can be determined realtime by MEA recording or calcium imaging. For calcium imaging, eyes of blind RCS rats will be injected with AAV encoding GCaMP3 and 5 to label RGCs with calcium indicators. To facilitate studies of spatial and temporal resolution, a micromirror display system will be implemented that will project pixelated images onto wholemount retina at defined refresh rates.

Methods

Imaging of Membrane Incorporation

Human embryonic kidney (HEK) and mouse adrenal chromaffin cells will be incubated with PVNs at 100 nM, 1 µM, and 10 µM concentration and examined with a fluorescent microscope to confirm that PVNs are anchored into the plasma membrane. The successful membrane integration of the PVNs will be indicated by membrane-localized luminescence (Rohan et al., 2013). Multiple incubation times (5 min, 1 hr, overnight) will be conducted to estimate the time required for PVN integration.

Membrane Potential Measurement in Cells In Vitro

Light-triggered membrane potential change will be analyzed with patch clamp recording. HEK cells will be plated onto glass-bottomed culture dishes 1 day before experiment. Cells will be incubated in physiological external solution (140 mM NaCl, 2.8 mM KCl, 10 mM HEPES, 1 mM MgCl$_2$, 2 mM CaCl$_2$, 10 mM glucose, pH 7.2-4, osmolarity 300-310 mOsm) containing PVN for 5-30 min (or the amount of time pre-determined by imaging experiments). Then cells will be washed and incubated with external solution with appropriate reducing (2-5 mM ascorbate, 100 mM sodium ferrocyanide) or oxidizing (100-200 mM potassium ferricyanide) agents for recording. Standard whole-cell patch clamp (EPC-9 amplifier, HEKA) will be performed, and cells will be patch clamped in current-clamp mode for measuring light-induced membrane potential change. Glass pipettes with resistances from 2-5 MOhms will be used. Patch pipettes are filled with intracellular solution (145 mM KCl, 10 mM NaCl, 1 mM $MgCl_2$, 1 mM EGTA, 2 mM ATP, 0.3 mM GTP, 10 mM HEPES, pH 7.2-4, osmolarity 290-300 mOsm). Membrane potential will be recorded before, during and after light exposure. Cells will be illuminated at the appropriate wavelength by a xenon lamp source through a bandpass excitation filter for 10-30 s with an irradiance value of 0.480 $mE/s/m_2$. The results will be subjected to unpaired, two-tailed Student's t-test for statistical analysis.

Action Potential Recording in Neuroendocrine Cells In Vitro

Action potential firing will be monitored in mouse adrenal chromaffin cells prepared according to established protocols, from 1-3 months old C57BL/6J mice, with perforated patch clamp in current clamp mode. Cells will be treated as described in membrane potential measurement in FIGS. 1 and 2. Perforating pipette solution will be freshly prepared by adding 1 µL of 125 mg/mL amphotericin B (Sigma-Aldrich, USA) stock solution in DMSO to 1 mL intracellular solution and homogenized for 5-10 s. Perforation is usually achieved within 3-10 min of gigaseal formation. Recording of action potential firing is performed after serial resistance drops below 25 MOhm. Light stimulus will be given as described in the membrane potential measurement.

Extracellular Recording of Single Cells with Multi-Electrode Array

Mouse adrenal chromaffin cells will be cultured onto the multi-electrode array and extracellular recording of field potentials will be recorded from 15 or 75 µM diameter electrodes using an MEA1060-Up amplifier and MC Rack software (Multi-Channel Systems). Cells will be incubated with PVN containing external solution for 10 min and washed with reducing or oxidizing agents for recording. Spikes in response to light stimulus before and after PVN treatment will be analyzed offline with Mini Analysis software (Synaptosoft).

Intracellular Recording of Leech Ganglion Neurons

Adult leeches Hirudo verbana will be obtained from Niagara Medical Leeches, Inc. (Westbury, N.Y., USA). Groups (20-30) of animals will be kept in glass aquaria with artificial pond water (36 mg/L Instant Ocean salts; Aquarium Systems, Mentor Ohio), in a temperature-controlled room at 16° C. and a 12:12 h light:dark cycle. At the time of experiments, leeches will weigh 1-3 g. Before dissection, the leech will be anesthetized in ice-cold leech saline. Leech saline has the following composition (in mM per liter): NaCl-115, KCl-4, CaCl2-1.8, MgCl2-2, HEPES-10, D-Glucose-5 (Sigma-Aldrich, USA). Individual ganglia will be dissected from the mid-body segments M6-M12, and pinned down in Sylgard-filled dissection box. Medial dorsal longitudinal incision will be made and the blood will be flushed away. Connective tissue and the blood vessel overlaying the ganglion chain will be incised. Dissected ganglia will be transferred to a Petri dish, pinned down in paraffin with six stainless steel pins (dorsal side up). PVNs will be microinjected into the extracellular space of the ganglion with a glass micropipette. Intracellular recording will be performed by penetrating the Retzius neurons with sharp glass electrodes (20-30 MOhm) filled with 3M potassium acetate.

Current clamp recording will be obtained using an intracellular amplifier AxoClamp-900A, digitizer Digidata 1440A and pCLAMP 10 software (Molecular Devices). Neuronal firing will be recorded before and after the injections.

Whole-Mount Rat Retina Recording

The retina will be freshly dissected from Royal College of Surgeons (RCS) rats (9 months' or older to ensure total loss of photoreceptors). The whole-mount retina will then be placed onto a multi-electrode array with the ganglion cell layer side facing the electrodes and is held down on the array using a lightly weighted porous membrane. Extracellular field potentials are recorded from 15 or 75 µm diameter electrodes using an MEA1060-Up amplifier and MC Rack software (Multi-Channel Systems). The activity of the retinal in response to illumination is monitored before and after PVN incubation. The retina is continuously perfused with oxygenated (95% O2, 5% CO2), heated (32C) Ames' Medium for baseline activity. The retina is then perfused with Ames' Medium containing PVN for 30 min to 1 hr, followed by 10 min wash with regular Ames' Medium before recording in Ames' Medium with 5-10 mM ascorbate. The retina will be illuminated by white LED light through a bandpass excitation filter (460-500 nm) with durations of 100 µs, 1 ms, 10 ms, 100 ms, 1 s and 30 s. Spike detection is performed offline with Mini Analysis software (Synaptosoft).

Therapeutic Efficacy of PVNs

Royal College of Surgeon (RCS) rats with retinal degeneration have a mutation in the merTK gene and lack the ability to phagocytose photoreceptor outer segments, resulting in photoreceptor death and loss of vision. They have served as a suitable model for evaluation of the safety and efficacy of various therapeutic agents. To investigate the effects of PVN injection visual functional evaluations will be performed in RCS rats that have been verified to lack apparent light sensitivity. Preliminary experiments performed using the above animal model showed robust light-induced activity during light stimulation in superior colliculus (SC) recording and pupillary reflex restoration from 2 hours to 3 days after a single intravitreal injection (see FIGS. 14 and 15).

These data demonstrate the ability of PVNs to restore light perception to animals, with photoreceptor-degeneration, at ambient light intensity (though some embodiments contemplate the use of an accessory device to amplify the signals). Acute and long-term experiments will be performed, with the acute study helping determine the optimum dose for long-term studies. Electrophysiological recording from SC will confirm the PVN evoked light response. Pupillary reflex will be examined before and after PVN treatment to assess the degree of functional recovery. Two behavior tests will also be performed, optokinetic nystagmus (OKN) and water maze, to investigate the spatial and temporal resolution from PVN treatment. Data obtained from the long-term study will reveal the persistence and efficacy of PVNs administration. Additionally, while data have shown that three days after injection, rats still exhibit visually induced superior colliculus light activity, it may be possible that the cells of the eye will naturally eliminate any membrane-localized molecule, the time course of which will be tested. Reducing that turn-over is addressed, in several embodiments, by use of a slowly dissolving delivery vehicle, such as a timed-release (and optionally biodegradable) hydrogel and/or a miniature ocular pump to facilitate repeat administration. In some such embodiments, the hydrogel is formulated as hydrogel particles, for example, polyacrylamide, cross-linked polymers, polyethylene oxide, polyAMPS and polyvinylpyrrolidone, or naturally derived hydrogels such as agarose, methylcellulose, hyaluronan (e.g., hyaluronic acid derived), polymethyl methacrylate, or HEMA (hydroxyethyl methacrylate). The form of the hydrogel varies, depending on the embodiment, and can be in the form of viscoelastic solutions, soft or stiff hydrogels, electrospun fibers, non-woven meshes, macroporous and fibrillar sponges, flexible sheets, and nanoparticulate fluids (among others).

Identification of Additional PVNs with Low Toxicity/Immunogenicity.

A range of candidate PVNs will be generated with the top candidates in terms of desired function (enabling rapid, light-induced membrane depolarization for the lowest light intensity at visible wavelengths, Aim 2) to be screened to rule out deleterious effects in vitro and in vivo. The data presented above importantly demonstrates an absence of signs of severe or rapid deleterious effects: rats whose eyes had been injected with Rubpy-C17 showed light-induced SC electrical responses up to 3 days after injection, and initial pathology studies revealed absence of obvious signs of deleterious effects.

Screening will identify the PVN candidates that show absent or minimal toxicity and immunogenicity, as these candidates would be attractive for translation to clinical studies. The in vitro testing will include: (a) Cell-based assay of growth inhibition (PVN concentration leading to 50% inhibition of cell growth). A recent data mining study showed that the inhibition of cell growth is a highly efficient approach to screening for deleterious drug effects—more efficient and cost effective than in vitro screening for cell death. The study found that cell line is not so critical, so HEK293T cells will be employed. In vivo testing will be conducted for different PVN concentrations and at different time points after PVN eye injection: a) Assay for apoptosis and necrosis in the eyes of rats injected with PVNs for the SC recording and b) Assay for lymphocyte and macrophage infiltration. The ideal PVN candidate will be non-toxic and non-immunogenic, and therefore will not cause significant inhibition of cell growth at the concentrations used for the therapeutic effect. It will also not show evidence of significantly increased apoptosis, necrosis, nor lymphocyte or macrophage infiltration, in rat eyes that have been injected with PVNs.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a photovoltaic nanoswtich" include "instructing the administration of a photovoltaic nanoswtich." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm."

What is claimed is:

1. A method of modulating the activity of an electrically excitable cell comprising,
    placing a transition metal tris(bipyridine) complex proximate to and/or in contact with the electrically excitable cell; and
    exposing the transition metal tris(bipyridine) complex to light energy,
    wherein the exposure to light energy induces a transfer of electrical energy and/or an electron from the transition metal tris(bipyridine) complex to the cell, thereby altering one or more of the trans-membrane potentials of the cell and the opening of one or more ion channels, thereby modulating the activity of the electrically excitable cell,
    wherein the transition meta tris(bipyridine) complex is represented by the structure of Formula (I):

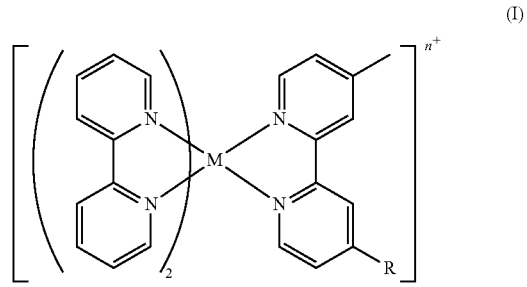

where M is rhenium, iridium, rhodium, ruthenium, osmium, platinum, gold, or palladium;
    R is an aliphatic fatty acid hydrocarbon pendant sufficient in length to anchor the transition metal tris(bipyridine) complex within the cell membrane; and
    n is 1, 2, or 3.

2. The method of claim 1, wherein M is ruthenium.

3. The method of claim 2, R is an alkyl chain and n is 2.

4. The method of claim 3, wherein R is a $C_{17}$ alkyl group.

5. The method of claim 2, wherein the ruthenium tris(bipyridine) complex is excited at the blue end of the visible electromagnetic spectrum and luminesce in the red end of the visible electromagnetic spectrum.

6. The method of claim 1, wherein the electrically excitable cell is a neuroendocrine cell.

7. The method of claim 1, wherein M is rhenium.

8. The method of claim 1, wherein M is iridium.

9. The method of claim 1, wherein R is an alkyl chain.

10. The method of claim 1, wherein R is a C17 alkyl chain.

* * * * *